(12) United States Patent
Dunn-Coleman et al.

(10) Patent No.: US 7,189,538 B2
(45) Date of Patent: Mar. 13, 2007

(54) HYPHAL GROWTH IN FUNGI

(75) Inventors: Nigel Dunn-Coleman, Los Gatos, CA (US); Geoffrey Turner, Fulwood (GB); Sarah E. Pollerman, Yorkshire (GB); Stephen D. Memmott, Lincoln, NE (US)

(73) Assignee: Genencor International, Inc., Palo Alto, CA (US)

( * ) Notice: Subject to any disclaimer, the term of this patent is extended or adjusted under 35 U.S.C. 154(b) by 134 days.

(21) Appl. No.: 10/778,804

(22) Filed: Feb. 12, 2004

(65) Prior Publication Data
US 2004/0224388 A1 Nov. 11, 2004

Related U.S. Application Data

(63) Continuation-in-part of application No. 09/275,549, filed on Mar. 24, 1999, now Pat. No. 6,995,239.

(51) Int. Cl.
C12P 21/02 (2006.01)
(52) U.S. Cl. ............... 435/69.1; 435/484; 435/254.11; 536/23.74
(58) Field of Classification Search ..................... None
See application file for complete search history.

(56) References Cited

U.S. PATENT DOCUMENTS

2004/0224388 A1 11/2004 Dunn-Coleman et al. .. 435/69.1

FOREIGN PATENT DOCUMENTS

| EP | 0215594 | * | 3/1987 |
| WO | WO 00/56893 A1 | | 9/2000 |
| WO | WO 02/079399 A2 | | 10/2002 |

OTHER PUBLICATIONS

GenEmbl database entry Z47158, directly submitted Dec. 16, 1994.*
*Ausubel, Frederick et al., "Short Protocols in Molecular Biology," Current Protocols in Molecular Biology, Chapter 9, Greene Publishing Associates & John Wiley & Sons, Inc., 1987.
*Benton et al., "Steering λgt Recombinant Clones by Hybridization to Single Plaques in situ," Science, vol. 196, No. 4286, pp. 180-182, Apr. 8, 1977.
** Berger and Kimmel, "Guide to Molecular Cloning Techniques," Methods in Enzymology, Academic Press, San Diego, CA, vol. 152, 1987.
*Carlile, M., "The Success of the Hypha and Mycelium," The Growing Fungus, ed. Gow. N. A. R. & Gadd, G. M., Chapman & Hall, pp. 3-19.
**Coombs, J., Dictionary of Biotechnology, Stockton Press, New York, N.Y., 1994.
*de Groot, et al., "Agrobacterium tumefaciens-mediated transformation of filamentous fungi," Nature Biotechnology, vol. 16, 1998, pp. 839-842.
**Dieffenbach et al., PCR Primer, a Laboratory Manual, Cold Springs Harbor Press, Plainview, N.Y., 1995.

*Erjavec, Z. et al., "Applicability of random primer R143 for determination of Aspergillus fumigatus DNA," Journal of Medical and Veterinary Mycology, vol. 35, No. 6, Nov. 1997, pp. 399-403, XP-000929979.
*Erjavec, Z. et al., "Aspergillus fumigatus putative vacuolar protein sorting homolog gene, partial cds.," Database EMBL Online Accession AF004837, Jun. 28, 1997, XP-002144970.
*Finkelstein, D., "Transformation," The Biotechnology of Filamentous Fungi, pp. 113-156, Eds, D.B. Finkelstein and C. Ball, Boston, Butterworth-Heinemann, 1992.
*Fungaro et al., "Transformation of Aspergillus nidulans by microprojectile bombardment on intact conidia," FEMS Microbiology Letters, 125:293-298 (1995).
**Glover, D. M. ed., DNA Cloning: A Practical Approach, MRL Press, Ltd., Oxford, U.K., vol. I, II.
*Grindley et al., "Conversion of Glucose to 2-Keto-L-Gulonate, an Intermediate in L-Ascorbate Synthesis, by a Recombinant Strain of Erwinia citreus," Applied and Environmental Microbiology, vol. 54, No. 7, Jul. 1988, pp. 1770-1775.
*Grunstein et al., "Colony hybridization: A method for the isolation of cloned DNAs that contain a specific gene," Proc. Nat. Acad. Sci. USA, vol. 72, No. 10, pp. 3961-3965, Oct. 1975.
*Hein, Jotun, "Unified Approach to Alignment and Phylogenies," Method in Enzymology, 183:626-645 (1990).
*Higgins et al., "Fast and sensitive multiple sequence alignments on microcomputer," CABIOS, vol. 5, 1989, p. 151-153.
*Kupfer, D. et al., "xlf08al.rl Aspergillus nidulans 24 hr. asexual development and vegetative cDNA lambda zap library Emericella nidulans cDNA clone Xlf08al 5', mRNA sequence," Database EMBL Online Accession Al212286, Oct. 20, 1998, XP-002144971.
*Kupfer, D. et al., "e4b02al. rl Aspergillus nidulans 24 hr. asexual development and vegetative cDNA lambda zap library Emericella nidulans cDNA clone e4b02al 5', mRNA sequence," Database EMBL Online Accession AA784458, Feb. 8, 1998, XP-002144972.
*Martinelli & J. R. Kinghorn "Aspergillus: 50 Years On," (1994) vol. 29, ed S. D., pp. 33-58.
*Martinelli & J. R. Kinghorn, "Aspergillus: 50 Years On," (1994) vol. 29, ed S. D., pp. 561-602.
*McGoldrick, C.A. et al., <<"myoA of Aspergillus nidulans encodes an essential myosin I required for secretion and polarized growth," The Journal of Cell Biology, vol. 128, No. 4, Feb. 1, 1995, pp. 577-587, XP-000530233.
*Memmott, S. et al., Abstract of Poster 339. "Morphological and genetic characterization of Hbr-2, a hyperbranching mutant of Aspergillus nidulans," 20th Fungal Genetics Conference, Online! Mar. 24-29, 1999, XP-002144968.

(Continued)

Primary Examiner—James Ketter
(74) Attorney, Agent, or Firm—Lynn Marcus-Wyner

(57) ABSTRACT

The present invention provides a method for producing desired proteins or chemicals in fungal host cells, which comprise modulating the nucleic acid encoding proteins associated with hyphal growth. The amino acid and nucleic acid sequences of hbrA and hbrB are provided.

36 Claims, 17 Drawing Sheets

OTHER PUBLICATIONS

*Pearson et al., "Improved tools for biological sequence comparison," Proc. Natl. Acad. Sci. USA, vol. 85, pp. 2444-2448, Apr. 1988.
**Sambrook, J. et al., Molecular Cloning: A Laboratory Manual, 2nd ed., Cold Spring Harbor Laboratory Press, Cold Spring Harbor, New York, 1989.
*Yarden, O. et al., "*cot-1*, a gene required for hyphal elongation in *Neurospora crassa*, encodes a protein kinase," >>EMBO Journal, vol. 11, No. 6, 1992, pp. 2159-2166, XP-002144969.
*International PCT Search Report. For PCT/US 00/07615.
International Search Report for PCT/US2005/004003 filed Feb. 9, 2005.

XP-002340229 retrieved from EBI accession No. EM_PRO:AY522343, Database accession No. AY522343.
XP-002340230 retrieved from EBI accession No. EM_PRO:CK448548, Database accession No. CK448548.
XP-002340231 retrieved from EBI accession No. EM_PRO:AB090888, Database accession No. AB090888.
Gatherar, I. M. et al., "Identification of a novel gene *hbrB* required for polarised growth in *Aspergillus nidulans, Fungal Genetics and Biology*," 41:463-471, 2004.

* cited by examiner

```
         10                    30                    50
GATCACCAGGAATTGCGTTGCCTGATGCATGGTTGGGAGGGCCGCCGAGGTCCACGCCAG
         70                    90                   110
GTGGTGGGGGTGCTATACCGTGCTGCGCTTTTGCCCTCGTGTAAGGGTCAGCAGGAATCG
        130                   150                   170
GTTTCGCGTAAGGATTCGCTTCGGCAGGAGGGCTCTTGTTCTTCGACCTCGATCCAAAGA
        190                   210                   230
GGGCGCGGCGGTTGGAGGAATCGTCGTCGCCGGCGTCTGACGACTTTTTGAGGCCGAATC
        250                   270                   290
GCTTCATAGCGTATTTTAGCTAGAATACTTCGCCGAAAcCAGCGTAGGAATAtTAGAGTG
        310                   330                   350
AAAATAATAAATTGAGAGGCTATTTATGATTGACTGAGAATTGAAGAGAGGGGAAGGGAA
        370                   390                   410
GGAGGGAGGGGAGCGAAGATGTTAAGTGTCAGGGGAGCAGCAGCGGCAAAAGTGTCAAGA
        430                   450                   470
CGCTCCTGAGACTCAAAGGCAGCTATGTAATCATGATACACATAGTTGTGCTGCAATTCT
        490                   510                   530
GGCTATCAGTGAGTATTTTACCGTATGATTACTCACCAATTCGACTCCACTAAGCCGAAA
        550                   570                   590
GAAGCTAGCGGGGATGGCTGGACCCTTCTAAGCCTCAACTGAGGGCGGTGCCGCAGTCAA
        610                   630                   650
ACGTCAACTGCTCCCACCCCATGCTTCGTATAAGGTAGCCATGGCACCATTCCCTGGGTC
        670                   690                   710
TGATGCCGACAATATCAAGGACAAGGCCCGTAAAGGCTTGCTGAATCTTCTCGAAGGCGT
```

*FIG. 1A*

```
                    730                   750                   770
                     .                     .                     .
       GAGTAAGGCTCCTAGTTGGCACTGTTTCTGGTTCTAGCCTGATTCATTACCTCGATCTAG 790                   810                   830
                     .                     .                     .
       GTCCGTGGGAAGAAGAACCTGGTGATTAGCCAGGGGCTTGCTGGGCCCGTCGGGCTTTTT 850                   870                   890
                     .                     .                     .
       GTCAAGTTTTCGCAGCTTCAGGAGTATGGCGTAGACCGGGTATTCTTGCTTGAAAATGGA 910                   930                   950
                     .                     .                     .
       AATGTCGACTCTTCTCAGCGCAATGTGGTATTTCTAGCGTACGCCGAAAAGATCCGCCAG 970                   990                  1010
                     .                     .                     .
       GTGCGGGCAGTGGCAGGTATGTCATGATCTTTATCCACCTTTGATTTACATACCCAAATG 1030                  1050                  1070
                     .                     .                     .
       ACTGTAAATGCGAAGGCTCCTTGCTATCGCGCTTGCTGGGAGCATTAAAGTTACGCAGAC 1090                  1110                  1130
                     .                     .                     .
       TTCTTCTCCACTCTGCGTAATCAGTCAAGCTCCCTATATTGAAACTTCGTTTAGCAGCTT 1150                  1170                  1190
                     .                     .                     .
       ATCCCTAAGGCTTTCTTTCTCTGCCTCGTATGACTGAATGCCATCAGAATAAGCTGACAA 1210                  1230                  1250
                     .                     .                     .
       GTTTTACAGAGCAGATCCAAAGGCTTAACGCAACAGCAGTATAGACCATGAATTTTCCA
                                                       H  E  F  S  I 1270                  1290                  1310
                     .                     .                     .
       TCTTTTGGGTTCCAAGACGGACCCTCGTAAGCAATAACATCCTAGAGAGCGCAGGCATCA
        F  W  V  P  R  R  T  L  V  S  N  N  I  L  E  S  A  G  I  I 1330                  1350                  1370
                     .                     .                     .
       TTGGAGATGTGAGCATCGCTGAGCTGCCTCTTTACTTTTTTCCTCTAGAGCAGGACGTTC
        G  D  V  S  I  A  E  L  P  L  Y  F  F  P  L  E  Q  D  V  L
```

*FIG. 1B*

```
              1390                    1410                    1430
                .                       .                       .
TTTCTTTGGAACTGGATGACTCTTTTGCGGACTTGTACCTGGTGAGATCTTTCTCCTGGA
  S   L   E   L   D   D   S   F   A   D   L   Y   L 1450                    1470                    1490
                .                       .                       . .
GATAGTGATCAGTGCTGATTCATTTTGTAGCACAAGGATCCTGGGTGCATCTTCCATTCC
                              H   K   D   P   G   C   I   F   H   S 1510                    1530                    1550
                .                       .                       .
GCAAAGGCTCTTATGgctATTCAACAGAGACATGGCTATTTTCCTCGGATAGTAGGCAAA
  A   K   A   L   M   A   I   Q   Q   R   H   G   Y   F   P   R   I   V   G   K 1570         .          1590                    1610
                .                       .                       .
GGCGATCATGCTCGACGACTCGCTGACCTCCTGCTGCGGATGAGGAAGGAGATTGACGCA
  G   D   H   A   R   R   L   A   D   L   L   L   R   M   R   K   E   I   D   A 1630                    1650                    1670
                .                       .                       .
GAGGAAAGCTCAGGACTGACAGGACTGTCTTTCCGGGGACTTTTACCCAGCTCAAGCATT
  E   E   S   S   G   L   T   G   L   S   F   R   G   L   L   P   S   S   S   I 1690                    1710                    1730
                .                       .                       .
GAGAGTTTGATCATCATTGACCGAGAGGTGGACTTCGGCACCCCTCTGCTTACACAGCTA
  E   S   L   I   I   I   D   R   E   V   D   F   G   T   P   L   L   T   Q   L 1750                    1770              ˙     1790
                .                       .                       .
ACGTATGAGGGTCTCATCGATGAGTTGGTAGGAATCAAGCACAACCAAGCGGACATTGAT
  T   Y   E   G   L   I   D   E   L   V   G   I   K   H   N   Q   A   D   I   D 1810                    1830                    1850
                .                       .                       .
ACGACAATTGCAGGGGCCAGCTCAACTCCCCAGGCCCAGGAGTCTTCCAAAGCATCTCAA
  T   T   I   A   G   A   S   S   T   P   Q   A   Q   E   S   S   K   A   S   Q 1870                    1890                    1910
                .                       .                       .
CAGGCTAAGCAAGGTCAAAAGCGGAAGATTCAGTTGGATTCGTCTGACCAACTGTTCAGT
  Q   A   K   Q   G   Q   K   R   K   I   Q   L   D   S   S   D   Q   L   F   S
```

FIG. 1C

```
              1930                    1950                    1970
               .                       .                       .
CAACTCCGTGACGCGAATTTTGCTATAGTCGGCGATATCCTGAATAAGGTAGCACGTCGA
 Q  L  R  D  A  N  F  A  I  V  G  D  I  L  N  K  V  A  R  R 1990                    2010                    2030
               .                       .                       .
TTAGAAACAGATTATGAGAGCCGTCATACAGCAAAAACGACAACTGAACTTCGCGAGTTT
 L  E  T  D  Y  E  S  R  H  T  A  K  T  T  E  L  R  E  F 2050                    2070                    2090
               .                       .                       .
GTGAATAAACTACCATCATATCAACTCGAACATCAAAGCTTGAGAGTTCACACCAACCTC
 V  N  K  L  P  S  Y  Q  L  E  H  Q  S  L  R  V  H  T  N  L 2110                    2130                    2150
               .                       .                       .
GCTGAGGAAATCATGAAAAACACGCGCTCAGACACTTTCCGCAAGATCCTCGAAGTGCAA
 A  E  E  I  M  K  N  T  R  S  D  T  F  R  K  I  L  E  V  Q 2170                    2190                    2210
               .                       .                       .
CAGAACGACGCTGCAGGCGCCGACCCAACTTACCAACATCCTCTCATTGAGGAACTCATC
 Q  N  D  A  A  G  A  D  P  T  Y  Q  H  P  L  I  E  E  L  I 2230                    2250                    2270
               .                       .                       .
GCCCGGGATATTCCACTGAAGACAATCCTCCGTTTGCTTTGTCTCGAATCATGCATGTCC
 A  R  D  I  P  L  K  T  I  L  R  L  L  C  L  E  S  C  M  S 2290                    2310                    2330
               .                       .                       .
GGTGGCCTACGGCCTAAAGACCTCGAGAGTTTTAAACGCCAAGTCGTCCACGCATACGGG
 G  G  L  R  P  K  D  L  E  S  F  K  R  Q  V  V  H  A  Y  G 2350                    2370                    2390
               .                       .                       .
CACCAACACCTGCTAACATTCAGTGCTTTGGAGAAGATGGAGCTTCTCCAGCCCCGGTCG
 H  Q  H  L  L  T  F  S  A  L  E  K  M  E  L  L  Q  P  R  S 2410                    2430                    2450
               .                       .                       .
TCTGCAACCACAATGCTAATTCCCGGCACGGGCACCCAAACGGGATCGAAAACAAACTAC
 S  A  T  T  M  L  I  P  G  T  G  T  Q  T  G  S  K  T  N  Y
```

FIG. 1D

```
              2470                  2490                  2510
               .                     .                     .
GCCTACTTTCGCAAAAATCTTCGCCTGGTCGTCGAAGAAGTTAGCGAGAAGGAACCTGAA
 A  Y  F  R  K  N  L  R  L  V  V  E  E  V  S  E  K  E  P  E 2530                  2550                  2570
               .                     .                     .
GATATCGCTTATGTCTACAGCGGTTTCGCCCCTCTCAGCATTCGCCTTGTGCAGTGCGTC
 D  I  A  Y  V  Y  S  G  F  A  P  L  S  I  R  L  V  Q  C  V 2590                  2610                  2630
               .                     .                     .
TTGCAGAAATCATACGTCATGTCGCTTATGAAAGGTGGCCCGGCTGCGCACGCGAATACC
 L  Q  K  S  Y  V  M  S  L  M  K  G  G  P  A  A  H  A  N  T 2650                  2670                  2690
               .                     .                     .
GCATCCCCAGGCTGGCTTGGATATGAAGATGTGGTGAAGAGTGCGCGTGGATCGACGTTC
 A  S  P  G  W  L  G  Y  E  D  V  V  K  S  A  R  G  S  T  F 2710                  2730                  2750
               .                     .                     .
AGTATTGTCCAAAAGGGCGACGATAAAGCGGTTCGTGCGCGGCAGACACTGAGTGGTAAC
 S  I  V  Q  K  G  D  D  K  A  V  R  A  R  Q  T  L  S  G  N 2770                  2790                  2810
               .                     .                     .
AATGCGGCTAAGACCGTGTATGTGTTCTTCCTCGGAGGGATCACATTTACGGAAATCGCG
 N  A  A  K  T  V  Y  V  F  F  L  G  G  I  T  F  T  E  I  A 2830                  2850                  2870
               .                     .                     .
GCATTGCGGTTCATTGCGGCACAGGAGGCGCCGAGGCGGAACATTGTGATTTGTACTACG
 A  L  R  F  I  A  A  Q  E  A  P  R  R  N  I  V  I  C  T  T 2890                  2910                  2930
               .                     .                     .
GGAATCATTAATGGAGATCGGATGATGGATGCTGCGCTTGAGAAGGGGGGGTTTGCCTTG
 G  I  I  N  G  D  R  M  M  D  A  A  L  E  K  G  G  F  A  L 2950                  2970                  2990
               .                     .                     .
ACTGAGTCTTGACCTCGTAGAGCGTACAGTTAATGTCATAGGAACTATACCGCTATCCAT
 T  E  S
```

```
hbra        . . . . . . . . . .  . . . . . . . . . .  . . . . . . . . . .  . . . . . . . . . .  . . . . . . . . . .  . . . . . . . . . .    0
afvac       . . . . . . . . . .  . . . . . . . . . .  . . . . . . . . . .  . . . . . . . . . .  . . . . . . . . . .  . . . . . . . . . .    0
ratvac      MAAHLSYGRV           NLNVLREAVR           RELREFLDKC           AGSKAIVWDE           YLTGPFGLIA           QYSLLKEHEV             60
slp1_yeast  . . . MNRFWN         TKKFSLTNAD           GLCATLNEIS           QNDEVLVVQP           SVLPVLNSLL           TFQDLTQSTP             56
slp1_caeel  . . . . . . . . . .  . . . . . . . . . .  . . . . . MAA        NEDRDDAAAI           LNWEGTSEIK           SANEYSRNLL             33 hbra        . . . . . . . . . .  . . . . . . . . . .  . . . . . . . . . .  . . . . . . . . . .  . . . . . . . . . .  . . HEFSIFWV              8
afvac       . . . . . . . . . .  . . . . . . . . . .  . . . . . . . . . .  . . . . . . . . . .  . . . . . . . . . .  . . HEFSIFWL              8
ratvac      EKMFTLKGSR           LPAADVKNII           FLVRPRLELM           D . . . MIA          ENVLSEDRRG           PTRDFHIL FV            114
slp1_yeast  VRKITLLDDQ           LSDDLPSALG           SVPQMDLIFL           IDVRTSLRLP           PQLLDAAQKH           NLSSLH I YC             116
slp1_caeel  FSVLDSLDGN           KTIVWDRDRS           VMHRVNLFAG           ASVLAAHGVV           ANHSIETKKS           ASTPHV V FFL             93 hbra        PRRTLVSNNI           LES . . . . .        . . . . . . . . . .  AG I IGD . VSI       AE . . . . . .       . . LPL YFFPL            42
afvac       PRRTFVSNKI           LED . . . . .        . . . . . . . . . .  AG I IGD . VNI       FE . . . . . .       . . FPL YEVPL            42
ratvac      PRRS L C EQR         LKD . . . . .        . . . . . . . . . .  LGV L GSFIYR         EE . . . . . .       . . YSL DLIPF           149
slp1_yeast  R W KPSFQNTL         EDTEQWQKDG           . . . . . . . . . .  PNVI H SQLKE         LSNEYTLYP W          . . DLLPF PQIDE         176
slp1_caeel   A . PTMVSLDL        LCD . . . . .        . . . . . . . YI     DNVRNDSYWE           RLESVKEIPL           . . CWLP . . . RDG      134 hbra        DVLYLSLELDDS         FADLYLHKDP           GCIFHSAKAL           MAIQQR . . .         . . . . . . . . . .  HGY FPRIVGKGDH          91
afvac       DVLSLELDDS           FGDLYLHKDP           GCIFLAAKAL           MDIQQR . . .         . . . . . . . . . .  HGY FPRIIGKGDH          91
ratvac      D L SL M ESESA       FKECYLEGDQ           TSLYHAAKG L          MTLQAL . . .         . . . . . . . . . .  YGT IPQIFGHGEC         198
slp1_yeast   N V LLTHSLYN        MEN V N M YYPN       LRSLQSATES            H L V D DMVNSL      QSLIFETN S I         ITN V S IGNL           236
slp1_caeel   E CLSLSSPQI         AARLL I NGDW         THLHKCAVAL           NQLIDMCRGR           SS . . SSNQR         PMSIY A KGKW           191 hbra        ARRLADLLLR           MRKEIDAEES           SGLTGLSFRG           LLPSSSIESL           IIIDREVDFG           TPLLTQLTYE             151
afvac       ARRLADLLLR           MRKELDAEES           SGLRGPSARG           LLPSASTESL           IIIDRMVDFG           TPLLTQLTYE             151
ratvac      ARQVA N MM VR        M K REFT G SQN       SVFPVF . . .         . DNL . . . .        L I DRNVDLL          TPLASQLTYE             247
slp1_yeast   S K RCSHLLK K       RIDEHQTEND           LFIKGTLYGE           RTNCGLEMDL           I L E RNTDPI         TPLLTQLTYA             296
slp1_caeel  ASDVAK MM G K        . MTKNLDP            IEGLLKINR I          V L IDRW M DPL       TP M LSQLTFY                               247
```

FIG. 2B

|  | | | | | | |
|---|---|---|---|---|---|---|
| hbra | YVMSLMKGGP | AAHANTASPG | WLGYEDVVKS | ARGSTFSIVQ | KGDDKAVRAR | QTLSGNNAAK 492 |
| afvac | .......... | .......... | .......... | .......... | .......... | .......... 430 |
| ratvac | ..ILFHNYSSQQ | ..SRPG | WRSIEEVLRI | LPGPHFEERQ | PLPTGVQKKR | QP...GENR 544 |
| slp1_yeast | ILFHNYSSQQ | PFILSREPRV | SQTEDLIEQL | YGDSHAIEES | IWVPGTITKK | INASIKSNNR 624 |
| slp1_caeel | .......... | .......... | .......... | ..EGDRVKWV | GWPKTVIGDK | SDLIAERDGR 530 |
| hbra | .......... | .....TVYVF | FLGGITFTEI | AALRFIA... | AQEAPRRNIV | ICTTGTIINGD 534 |
| afvac | .......... | .......... | .......... | .......... | .......... | .......... 430 |
| ratvac | ..RSIDGSNGTF | ..VTLVF | FLGGVTFAEI | AALRFLS... | QLEDGGTEYV | IATTKLINGS 586 |
| slp1_yeast | .......... | ..HAAEDIALVV | FLGGVTMGEI | AIMKHLQKIL | GKKGINKRFI | HIADGLINGT 684 |
| slp1_caeel | .......... | ...GTCVF | VIGGLTRSEL | AIIR...... | .ENLPNVAL | ITTSALITGD 567 |
| hbra | RMMDAALEKG | GFALTES | 551 | | | |
| afvac | .......... | ....... | 430 | | | |
| ratvac | .SWLEALMEKP | F*..... | 597 | | | |
| slp1_yeast | .RIMNSIS.. | ....... | 691 | | | |
| slp1_caeel | KLLNNITN.. | ....... | 575 | | | |

FIG. 2C hbr3 Nucleic Acid Sequence (SEQ ID NO:___)

```
TTTTTNGGGG GNNCCCCGAA ACCNAAATTT TTTTTTTTTA AAAAANNCCC    50
NCAAAGGGGC CCAANAAAAA AAAATTTTTT TAAAAAAAAA ANCCGGGATC   100
CCNGGGCCAA AATTTTGGTT CAAAGGGGNC CCNACCCCNT NCAAAACCCC   150
CGGNCGGGAA ANTTTNTTTA TTNCGGGCAA AGGGGAACCG GAATGAAAAA   200
ATTNGTCCAA AGGGTCCAAA GGGCAATTTT CCCCNTTTN CCCCAAAAAA    250
AACCGGGGTT GNNCAANGNG TTTTTTTNCA AAAAAAAAAA ANTTGGGNGG   300
GNAAGNNGTT AAAAAAANTG GTATTTTCCC TTAANGTAAA NGTTTTGGGT   350
TTGGCCCCNT TTCCATTTTC CCTTTGGGNG GGTTGGNCTC AAGGGGGTCC   400
CCCAANCCAA AAACCTGTTT GGTACATTTT TAAGGCCTTG TGCCAAGTTN   450
GCANGGTCCC TCGACTTTCG GTGAANAGGA ATCGGTCTCG GTTAAAATAN   500
AATTCCCAAG CTTCCTTGAT AATGTGGGTT TTGATTGTTG ATTCATTTGA   550
NANAGCGTGT TTGNATTTTC GCTTGTGTTT TCGAAATTCA TATAGNACTT   600
GGTGTGATAG GGCGGGTCTT TCGTTCTTGA TACCCAGGAT AGTGAGACTA   650
CCCAAGGATT CACTATTTCT TCTTCTTCGG ACACCTTTCA CTGGCTTGGT   700
GTATCTACTC CCATGTAGCA GCAGGCGGCT CATGCATCGT CATCAACCAC   750
TTCCTCTCCG TAGTTCTCTT CCTCCTTGGC TTCATTCTCT GACAATTGGC   800
GGCCCTGGGC TTCAGCTGTT TTCTTGTCCA CCTCCATACG TTCGGTCAAA   850
AACAAATTGA TGTCATTCTG TAGCGCGGGA ACCAGTTTTC GAAGCTCCGA   900
GAGATAGGTG ACTTTGACTT TTATGTTTTC CTCTGAGGGG CTTGGTGCGG   950
GTGAGTTGAT GGTGTGCTCG AACGTGCGGT TCAGCTGAGG CGAGGTGTAT  1000
TGGGCCTGGA GCCGATACGA CTGAGATGAG GATGTCGACG CCATTCTGAA  1050
TATCTGCTAG CCTGTTGTTC TTGAAGCTGC TATTCAGGAG GGGAAAAGAG  1100
GAAAGAGGGA GAAATTGATG GCGGGGCGAG CTAGCAGCGG GAGTCAGTCC  1150
AGTGTTGCGG AGCAGACAAA CGATCGACAG GAATACCTAA CGATCGCCTG  1200
GCCGGCTGGT CTTCTAGGCT ACTGTGTTAA TCTCTCTGGA ATAGATTCGA  1250
ATCATCAGAT CCAAATCAGT CAACATGACA ATGTCTGCAT AGTGAAGAAT  1300
GAACTCCTTG CTGTCTTGAT TACATACTCA GCCCCGAACC TCCACCGGCA  1350
CTGCCCGCTG CTGGAAATGC TGCGCTCCCC CGTCACCGTC TCTCCAGAGC  1400
GCTCAGCCTC TCGACCACCG CTCCCTCGTT CCTCTTCTGA CTTCGATGAC  1450
GACCCAGACC GTCCAGGCTC CTCCGGAAGT GATGCCTCGT CGGTGATCTC  1500
AAATGCGACT GCATTCCAAA CCACCCCTCA TCGCCGCGAC CGCGACCGCG  1550
ACCGCGAACC GGATCCGTCC TACTCCCCTC GTACCGTTCT TCGGACACCA  1600
CCCACCGAAA CTTCAGCCGC AGCCTCAGCC TCAGCGCAAG GCCCAGGGCA  1650
TCCCCCGACT TCATTCATGC CGCATCATGA TCCTACGAGC AGAAAGCCGT  1700
CTGGACGAGT CTACCCGTCG GACCTGCACA AGCGCTCGCG GCACCACTCG  1750
CAGGGGTTCT TCGAGCCGTC CCTGCCCACG GCTTCGTCAT CTGACGCGAC  1800
GCTTTCAGCG TCTAGGATAG CAGCTCAGGC TGGTATGCAA AGCCAGGGTC  1850
AGCATTCGTC TTCTACGATC CCTCAGGTTC CTCCGAAACG GGCTGTGCAG  1900
GGACATGGTT CAGACAACGG GTCAGGATCG GTCTCACCAC CTCCCCCGAT  1950
TCCGGCTTCC CAGCCGCAGA GACCCGGGTC TGCAGGCTCG CCATATCACA  2000
ACTCGAATGC CACTACCGGA GGGCATGGTG TAGGGCAGGC TGCGGCGACG  2050
ACGGCTGCCA ACCATGTCTT TCCACGGCTA CCGCCGCCGG GAGTGGAAGC  2100
ACATCCTAAT GAGCGAGAAC ATAAGAAGAC TGAGAAGGAG AAGTCGAAAA  2150
TGAAGCTTTT TTCGAAGCCG AAGCATATTG GCATCAGTCG TGATAAGGAC  2200
TTTAAGGACA GGGGACTCCC GTCACCGAAC AAGATTTCCG GGCTGACACG  2250
GATAGTCAGT GCGTCTGCGA CGAATCTTGC GGATATCTAT CCGTCGAATA  2300
ACTCGTCTAT GTATAGCCTG TCAATGCAT CGGCGAGCAC TGTTGTACCG   2350
GCTGATAAGC CTTCGGTACC TGAGAAAGAG AAAGACAAGG AAAAGGACAA  2400
```

FIG. 4A hbr3 Nucleic Acid Sequence (SEQ ID NO:___)

```
AGAAAAGGAC AAGGAAAAGG CCCACCGGCA TCATCATTTC TTGTCGCGGC    2450
AGAAGCTGAA GCTGAAGGAT TTGAAAGATA AAGATGATCA TTACAACCTG    2500
CCGCTCTCTT CTCCGGCGAG TAACTCCAGA CCGTCAGACC CTAATGCTCC    2550
GCAGTCACTA TACTCTTTCA CTCCGGCTTC CCGAGTGCT  ACTACTACTT    2600
CTTTCAGCAA GTCTGTAGGC GGGTTGGATC TATTACATGG TGGGCGAGCG    2650
CTCCGCGACA AGAAGAAGGA AGAGAAGACG CTTGCAGAAG AACAGCCGGA    2700
ATGGTTGGCG AATTCGACAG TCGCTGGGGC AGCTACTGCA GGGTTTGCTG    2750
GGCCGTCATC GTTAGGAAGT ACTGGGGGCT TCCTCACTGA GGCTGTTGTA    2800
CGGGAAACGT ACAAGGCTT  TGGTCTTCAT AATATGAGTC CTGAAGATGC    2850
ATGGACTTC  TTAAAAGCAA AACTGTTGGT GATTTTCGAC GGCGAAGATG    2900
TTCGCATTGC AATTGAGGAT CTGAACAAAC TAGTGATCAT CCATATTCAG    2950
CGCTGCGTGC AGAGGCGTAC GCCGACAGCT ATAGTCGACG ATCTACGCGG    3000
GCTGCTGGAA GCTGGCTTTG CCACCTTGAA CCATACCCTC AACGGCGTAC    3050
CGGATGATAA GCTGGTGCCC CATCTCGTGC AGATCTGGAT GCTAGTATTT    3100
GGCACCATTC TCCCTTTCAT TCAAGCCGTC TTCCTACCCC TAGATCTTGA    3150
ATTCAAAGGC TGTGGCTCCG TCATGAACAT ACGAGAAGCA AAGAACTTCT    3200
GGAGCCTCGC GCTAGATGGG GAATATCCCG GTTGCGAGCT CGAAGTCCGC    3250
AACCTCGTTC TTATCGCCTT CCGCGACATG GTCATCATCA ACCGCTACGA    3300
TAACCTCAAA GCCACCTTCT CCCGCTTGAG CCTTGACAGC ATCAAGCTCG    3350
GCAACTCCGC CCTTAGCGTA ACAACGAAAA GCAGTAATAA TAGCAATAAC    3400
GGCCGCCCTA CGACCTCCGC ATCCTTCGAC GGCGGGTTTG GCAGTTACAG    3450
TTCCCAATCA TCCACCTTCC TAAATACAGC CGGCAGCTTT TCTTCGGAAT    3500
CCCCAGGATA CAACCGCAGT CGTGCTACCT CCAACACCTC CTCAAACCCC    3550
GACCAACTCA TCTTCCAATC CTTCTCTTCC CCTTCTCAAC GGCCCACGAT    3600
TATCCACCGC GCAAACAACG CATCAGATAC ATCTCACGTC ATCACCGAGA    3650
CAGTCGGCCG CATGCTCCAG TGCATGAGTG TCCTCGCAAG TGTGCAGACC    3700
AACGATACTG CGCAGGAACG AATTGAGACA CTCAGCAAAG ATCTCAAGCA    3750
TAACTGGTTG GGACGCGGCC GGACAGGAAG AGATAGGCGT GGTTTTGTGG    3800
GGACGAAGAT TCGCCCGCCG ATCGTTGCAC AGGCGAGCGA TAACTCTACT    3850
GATTCTAATA TGGACGAGTT GAGTTCCAAG AGGTTGCAGC AGGAGTTGAG    3900
TGTTTTGTGA TGTGAAGATA TCGATATCTT CTCTTCGTAG ATTGGTTCAC    3950
TCTATAGCAC TTCGTTGTTT GTCTGGTACA AAGCAAGGAT TATGTGTCTC    4000
AGCGCGGACT TTTATCTATC CTCTTATCTC CATTTATTGT TCTGGGTTGG    4050
TGCAGTGGGT TCGTGGGTTT TGGATTGAGT TCTGCTGGCG TTCAATAGGG    4100
CTACATAGGA GCGAATACTA CAAAAATCAA GTGAATCGCG CGTCAAAGCA    4150
TTCATATCTG CTCTCCCTGT TCGAGCTAGT GACAAGTTCC AGAAACCACC    4200
TCGCCGGCAG CTCTAAGTCC AACCTACTCT GTGTTTGTAT TCATCCACAG    4250
ATCATCAAAT AAGTCAATCT TACACCCTCA GATGTTAATG TCATCCGGGT    4300
TTCCGGATCA TGATAACGCC AAAGACTTCA GCCAATCTTT TCAGGGCATC    4350
CAAATAAGCG AAATGAAATA CACGATAGGA ACGAAGACAA ACTCCTAGAT    4400
AAACTGCATG CAGGTAGAAT CTCTTCGCTC CGATCTACTC CTTAGTATCA    4450
TCAGTCCCAA AAGCTGCTTC ATGAGCAGAT GTAGCAGCGT TCTTGCTCAA    4500
TTCCTTGAAC TTCTTCTGGA GCACGGCAAT AGGATACTTC TCCCCGCCGT    4550
CGCTCTGAAT CGCCTCCATG ATACGATGCC ACTTTTCCTG CTCGAATTTG    4600
TCCTCAATCT CCTTTTTCAA CCGGAGAAGA CGTGCTTCCT GCGGCCAGTT    4650
AGTGTTGATG TCAGCAATCA GGCTATTGCT ATCCGGGGTG TGGTGTGATT    4700
```

FIG. 4B hbr3 Nucleic Acid Sequence (SEQ ID NO:__)

```
CAGGGTAGCC AGACATACAT CTTCGATCGT GATCCCCACA AAATTCGCCT   4750
TCATAGTACT CCAGCGTAAT CTAAGTGTCG TACTACCGAC CTTGATCCCC   4800
GTTTTCTCAG TGAAGAGCCT GTTGATCTGC GTCCATGGCT GCTTTTCCTC   4850
GTCGCGCAGG TGTAGGATCA TACGGTCCAT TTCACCCGCT GTTGCAAGGC   4900
TGGTTGGGAT GGGGGGAAGA GTTGCGCGGG CTGGTGCTCC TTCCGGTGTA   4950
CCAGTGCCAT TTCCGGCGAC AACCCCGGTA TCCTTCTTGG ATTTCTTAGA   5000
AGGGGTTTTG GGGAGGCGC  GCTTGCCAGT GCGCTTGCCG AGTTTAGGGG   5050
TTTCTTTTTT GGTCATCGAC ACTGGCGAGG CGTTGGTGTT CTGGAAATTA   5100
TTCGTTAACT CCGCTTTGTG TTTGTACAGT AGCGGATATG GTTACTGACT   5150
TACGTTTTCC TCATCTTCTG CTTCGATGCC GGATAGAGGC TGCTCATCCC   5200
CGTTGTCGTT CGCTTCATTC ATCGCTGCAT TGGCAACTTC CCGTCCGTGG   5250
TCGGTGCGGA TATTTATGGG GGTGAACTCA ATGGAATGGG TGGATAGTTC   5300
TGTACTGATG TCGAAGTCCA TACTTGAGGT GATGAGAAGC TGATATCTTC   5350
TTGTCGTGGA CGTTAATAGC TAGTTTCGAC TAAGGTATGA GAAGCTCGAG   5400
GGTTGAGTGA AGATGAGCGA GCGGATACAG AAACCCAGGC TTGACTGACT   5450
ACAAGCTTGA ATGAGAAATC AGGGAAGTGA ATTGAATGAC TAGATGGAGG   5500
TCACGGTTTG GTGTGAGGGC TAGAGATGAA CTTGAGTTGG TGCAGGAAGA   5550
TGAACGAGCA GGATGTAGGA GGGTAGAAAA ATGGCAGTAT GATTCCTCAC   5600
TTGGAGAAGA GGAAGAGTAC ACCATGAAGT CAAGAAGTGT TGCTCCTAGT   5650
TGAGGTGAAA CGCTGGGAAG AGCGAGGAGA CTTCGTTTGT GTTGGTGATA   5700
TTGAGTGAGC ATCATCAGGA GCTGCTTCTT GGACATGCCG CTTATGTTTA   5750
CGAAATAAAG AGATAAATAT ACTTTAATGA TAGACTCAGA CTCTGGTACA   5800
TACTCCACGG ATTTGGTAAC ATTGAAACTA TACTGAACTT CATTCGCGTG   5850
CCATGATTGT CATTCGATTC CAGGTCCATA AGACGAAGGA TTGCTAGTAG   5900
GCTACAGGAA CTAGTCATAA TAGCAGCGGT CTGGGCTCTG GTTACAAAGA   5950
CTAATGCGTT ATTTATACAA TACAGATCTC TGGCCATGGA ACTACGCTGC   6000
ACTGCTATCA GCTTGCTCCA TGTCTTGGGA AACATACCCT AAAGGCTCTG   6050
GCTGAGTGTA AGCGCGGTAC TAACGCCTTA TTAATGCTCT ATACTCCAAC   6100
CAGCATGATT GGCACTGACA AGATGCTGAC GGTGAATTAG CAAAGCATGA   6150
AAGCTTGCTT GCTTCTTCGT ATACAGTTTG CTGTTTGATG ATTCGATTCT   6200
CGACTAAAAA AGTGAAGCGG CATCCTTCAG CTCTCGCCCG AGTTGCGATT   6250
CATTAATCGC ACGATTGATT CGGATGCTCA GTTGTTGTGT CACATGGTTG   6300
AAGATAATCA CTGATCCTCA TCTCGATCAA CTCCATCGCC GGCTGGACCA   6350
AACTGCTCAA TCGGTTTCTG AGGTCAGTGG GACTGACCGT TGAGACGATC   6400
GATTTGTCCG AGCCAACACA CATCGTGACC TGAAATATCC CACCTTGGTA   6450
GTTACACTAA AGGGCTCGGC AGCGCTCAGT CCATAGACTG ACAAGAAAGC   6500
ATTGGAAGA  AGTACCTGCA CTAACCCTGA GAACTGACAA CTCTGCATGC   6550
AAACCGGGCA ACGCCATTCG CCAGCTGTGC TCCATCGTCC TTAGCTGCAG   6600
TTTCTTCTGG GAACTTCGCG ATCCGCGGCC GGGGATCCA  CTAGTTCTAG   6650
AGCGGCCGCC ACCGCGGTGG AGCTCCAGCT TTGTTCCCT  TTAGTGAGGG   6700
TTAATTTCGA GCTTGGCGTA ATCATGGTCA TAGCTGTTTC CTGTGTGAAA   6750
TTGTTATC                                                6758
```

FIG. 4C hbrB3 Protein Sequence

```
MLRSPVTVSP ERSASRPPLP RSSSDFDDDP DRPGSSGSDA SSVISNATAF  50
QTTPHRRDRD RDREPDPSYS PRTVLRTPPT ETSAAASASA QGPGHPPTSF 100
MPHHDPTSRK PSGRVYPSDL HKRSRHHSQG FFEPSLPTAS SSDATLSASR 150
IAAQAGMQSQ GQHSSSTIPQ VPPKRAVQGH GSDNGSGSVS PPPPIPASQP 200
QRPGSAGSPY QNSNATTGGH GVGQAAATTA ANHVFPRLPP PGVEAHPNER 250
EHKKTEKEKS KMKLFSKPKH IGISRDKDFK DRGLPSPNKI SGLTRIVSAS 300
ATNLADIYPS NNSSMYSLSN ASASTVVPAD KPSVPEKEKD KEKDKEKDKE 350
KAHRHHHFLS RQKLKLKDLK DKDDHYNLPL SSAASNSRPS DPNAPQSLYS 400
FTPASPSATT TSFSKSVGGL DLLHGGRALR DKKKEEKTLA EEQPEWLANS 450
TVAGAATAGF AGPSSLGSTG GFLTEAVVRE TLQGFGLHNM SPEDAWDFLK 500
AKLLVIFDGE DVRIAIEDLN KLVIIHIQRC VQRRTPTAIV DDLRGLLEAG 550
FATLNHTLNG VPDDKLVPHL VQIWMLVFGT ILPFIQAVFL PLDLEFKGCG 600
SVMNIREAKN FWSLALDGEY PGCELEVRNL VLIAFRDMVI INRYDNLKAT 650
FSRLSLDSIK LGNSALSVTT KSSNNSNNGR PTTSASFDGG FGSYSSQSST 700
FLNTAGSFSS ESPGYNRSRA TSNTSSNPDQ LIFQSFSSPS QRPTIIHRAN 750
NASDTSHVIT ETVGRMLQCM SVLASVQTND TAQERIETLS KDLKHNWLGR 800
GRTGRDRRGF VGTKIRPPIV AQASDNSTDS NMDELSSKRL QQELSVL    847
```

FIG. 5

Alignment of A. nidulans hbrB3 with A. fumagutus and N. crassa homologs

```
A.nid      -------MLRSPVTVSPERSASRPPLPRSSSDFDDDPDRPGSSGSDASSVISNATAFQ
A.fum      -------MMLRSPIPPERTSSRSPAPPRPSFDDELERPGSAGSDASSVASNVTTVS
N.crassa   MGLVRPHRPSPGPVRIISASTSTSDDLTPLTIPRPSDQPTAPSPQPGGRPDASGFGGRAG A.nid      TTPHRRDRDRDREPDPSYSPRTVLRTPPTETSAAASASAQGPGHPPTSFMPHHDPTSRKP
A.fum      AIQSSLNNF----GAAPDASSPRIPRTSSTNGSGTTDDNPRRPSASSLMPQNEMTSRKI
N.crassa   ASPERRGGGGTTPTPGRESATPIYSSFTSPSNSASAPSLQTNFSRPTVSTTAALSTARSV A.nid      SGRVYPSDLHK-------------------------------RSRHHSQGFFEPSLPTASS
A.fum      SGRVVPPDLSRH------------------------------RPRHHSQGFFEPSLPTASL
N.crassa   AGTLSPIDTAPRNGPSPLTLPPTSATSTTSTSFSGRVGVHSRKHSANAGLFEPTLPSTST A.nid      SDAT-----------------LSASRIAAQAGMQ-------------------------
A.fum      SDVT-----------------LSASRIAAQAAMQ-------------------------
N.crassa   SNLDQIQAESPKLSPTPSQAQRDMSASHIAAQAAVSKSQLTQQQQQQPQQQQQQQQQQQQ A.nid      ---------SQGQHSSSTIPQVPPKRAVQGHGSDNGSGSVSPPPPIPASQPQRPGSA
A.fum      ---------QQSSAAQHPPKRLPSNVQGPDGRGGSISPPLPPPQQVLAAPGSGSTSG
N.crassa   APPFAHQHLVHLQHRQRSQTIPPSGEHHEQTSVANKRKSGGPMSPPILSLTEASAPRDNV A.nid      GSPYQNSNATTGGHGVGQAAATTAANHVFPRLPPPGVEAHPNEREHKKTEKEKSKMKLFS
A.fum      QS---YQNGIVGGNALAATTAANVVFPRGPALQPGMASDQAQPEREQKQKGDKPKMKLFS
N.crassa   FGSQGNHNGLAGNHTLAATAAANVVFPRSAQSSPKLPAQPTNPLTPTPPVAAEKPAVKS
```

FIG. 6A

Alignment of A. nidulans hbrB3 with A. fumagutus and N. crassa homologs

```
A.nid     KPKHIGI-SRDKDFKDRGLPSPNKIS---GLTRIVSASATNLADIYPSNNSSMYSLSNAS
A.fum     KPKHIGI-SRDKDSYGKDKGIPSPSKMGFPGSSGLSRIVSGSTDTLPSNNSSMYSLSNAS
N.crassa  EKSKVKLFSRPGKSSSKAESSKEKPLPSPGKLGHAFSNLQRANYSTTSLESNMQQPFYAH A.nid     ASTVVPADKPWVPEKEKDKEKDKEKDKEKAHRHHHFLSRQKLKLKDLKDKDDHYNLPLSS
A.fum     VNTVVPADRQASSEKDKDKDKAHK-------HHFLSRQKLKLK---DRDDHYNLPLSS
N.crassa  GNSSTATIRPAEATEKEVKEKEKK-------HGHFLKRQKEKLI------EAYHLPLSS A.nid     AASNSRPSDPNAPQSLYSFTPASPSATTTSFSKSVGGLDLLHGGRALRDKKKKEEKTLAEE
A.fum     ASSNSKPSDPNAPQSLYSFTPASPNAGSTTFSKTVGGLDLLHGGRALREKKKEEKLREEI
N.crassa  ASSNSRPTDPTAPSSLYNFNLPTSPGPSSNAFKS--GLDLRHGGRALREKKNKEDKSLDD A.nid     QPEWLANSTVAGAATAGFAGPSSLGSTGGFLTEAVVRETL---QGFGLHNMSPEDAWDFL
A.fum     EQDLV-----VSCATPAVFSGPSSLGNSTGLLPEAALRETL---SGFGLHNMTPDDAWDFL
N.crassa  AASSY-------NPGGDWPGPSSVSSATGNLASALFHNEPFDSQKFGLNNMTLDDAWPFL A.nid     KAKLLVIFDGEDVRIAIEDLNKLVIIHIQRCVQRRTPTAIVDDLRGLLEAGFATLNHTLN
A.fum     KAKLLVIFDGEDVRIAIEDLNKLVLIHIQRCVQKHTPTAIVDDLRELLETGCASLNHTLN
N.crassa  RAKLLVIFEAEDLRLPVEDLNRIVTMHIQYCISRRSPNIIIEDIRDFLTTGFSSLDQSLK A.nid     GVPDDKLVPHLVQIWMLVFGTILPFIQAVFLPLDLEFKGCGSVMNIREAKNFWSLALDGE
A.fum     GVPDEKLVPHLVQIWLLVFGTILPFIQAVFLPLDLEFRGAGSVMNLREAKDFWNSVPTGK
N.crassa  KTPEDRLIPALVELWIFTFTSILPYLQAVFLPLDMEFAGNGPLMTPDQARDFWGGVPASY
```

FIG. 6B

Alignment of A. nidulans hbrB3 with A. fumagutus and N. crassa homologs

```
A.nid     ----YPGCELEVRNLVLIAFRDMVIINRYDNLKATFSRLSLDSIKLGNSALSVTTKSSNN
A.fum     ----DFENELEVRHLVLVAFRDMVILKRYEGLKATFSRLSLDSINVGSSALSITTKSSNN
N.crassa  GLSISASSVLDIRRLVLLAFRDIVILPRYDTLKIMFSRLSLEFLPQSLASMALSSPVPVP A.nid     SNNGRPTTSASFDGGFGSYSSQSSTFLNTAGSFSSESPGY--------------------
A.fum     S--GRPATAASLDAGFGSYNSQSSTLLNTAGSYSSDSMS---------------------
N.crassa  TSGFQNTAHNQGGAYQPALSTSPSQESQLSLSFAGSLPATMTLGMGAGFGTAPPRPNTSM A.nid     --------------------------------NRSRATSNTSSNPDQL-----------
A.fum     --------------------------------NRSRAASNTSSNPDQL-----------
N.crassa  SNPVPSVDPSYASYNSNGMGTAGGGGDTPPGSGNRSRTISNVSFGSDHGNANRPFTPSSI A.nid     ----------------------------------------IFQSFSSPSQR--------
A.fum     ----------------------------------------IFQSFSSPNQR--------
N.crassa  QALGAASAQAAMSTPSGVGIANLNLNMSTPVQQFPLHVAPSIASIGSNSIHGSLRDPTGG A.nid     PTIIHRANNASDTSHVITETVGRMLQCMSVLASVQTN-----------------------
A.fum     ATVIHRASHTADTSQLITETVGRMLQCLSVLASVQTG-----------------------
N.crassa  GGGGRTADQNVEDSKQVTEMVGRMLQCMSVLASVSAPTTPSFTSSIPNQNPHSSTGNLTS A.nid     ------------------------------------------------------------
A.fum     ------------------------------------------------------------
N.crassa  YNTYSSSQDSVATTTMTNATVPASPSGSSVAGGLPPLVQTMSSPSQFSSPSSPATPTANS
```

FIG. 6C

Alignment of A. nidulans hbrB3 with A. fumagutus and N. crassa homologs

```
A.nid      ------------------------------------------------------------
A.fum      ------------------------------------------------------------
N.crassa   PGPLPPRPSISSLSASLATSGISGAGNNSLPNTPTAANATTPTTPTAPANAAAGGGGGGG A.nid      ----------DTAQERIETLSKDLKHNWLGRGRTGRDRRGFVGTKIRPPI
A.fum      ----------DEAQEKIETLSKALKHNWLGRGRTGRDRRGFVGAKVRPSI
N.crassa   GGGGAGGPGGGTGGYGNVPPDESSRMIEELNKLLKLNWLGRGRTGRNRRGIVGGRVKRAG A.nid      VAQASDNSTDSNMDELSSKRLQQELSVL---------------------------------
A.fum      TTHTTSDDSMNDPRNSDLGWQIHEGRQQVSVL--------------------------
N.crassa   AGSGSGSALAFSMGAGSAGMGYASSSSYGGYAGQGGGGGGGGGGGGGGYAGSLGTG A.nid      ------------------------------------------------------------
A.fum      ------------------------------------------------------------
N.crassa   PAGVSMNSLGTTGTMGSMMSIGTVGSGFGGGLLQGQQAERDRGGGGWTGTGTGSGLGTSA A.nid      ------------------------------------------------------------
A.fum      ------------------------------------------------------------
N.crassa   SIIAGTTGTGGMMMSSLPIGASVSATTAGTVGAGAALAGAAGVSMPAAAAGSLSNEIVVD A.nid      -
A.fum      -
N.crassa   N
```

FIG. 6D

SEQUENCE LISTING

```
<160> NUMBER OF SEQ ID NOS: 11

<210> SEQ ID NO 1
<211> LENGTH: 3000
<212> TYPE: DNA
<213> ORGANISM: Aspergillus nidulans

<400> SEQUENCE: 1
gatcaccagg aattgcgttg cctgatgcat ggttgggagg gccgccgagg tccacgccag      60
gtggtggggg tgctataccg tgctgcgctt ttgccctcgt gtaagggtca gcaggaatcg     120
gtttcgcgta aggattcgct tcggcaggag ggctcttgtt cttcgacctc gatccaaaga     180
gggcgcggcg gttggaggaa tcgtcgtcgc cggcgtctga cgacttttg aggccgaatc      240 gcttcatagc gtattttagc tagaatactt cgccgaaacc agcgtaggaa tattagagtg     300
aaaataataa attgagaggc tatttatgat tgactgagaa ttgaagagag gggaagggaa     360
ggagggaggg gagcgaagat gttaagtgtc aggggagcag cagcggcaaa agtgtcaaga     420
cgctcctgag actcaaaggc agctatgtaa tcatgataca catagttgtg ctgcaattct     480
ggctatcagt gagtatttta ccgtatgatt actcaccaat tcgactccac taagccgaaa     540
gaagctagcg gggatggctg gacccttcta agcctcaact gagggcggtg ccgcagtcaa     600
acgtcaactg ctcccacccc atgcttcgta taaggtagcc atggcaccat tccctgggtc     660
tgatgccgac aatatcaagg acaaggcccg taaaggcttg ctgaatcttc tcgaaggcgt     720
gagtaaggct cctagttggc actgtttctg gttctagcct gattcattac ctcgatctag     780
gtccgtggga agaagaacct ggtgattagc cagggggcttg ctgggcccgt cgggcttttt     840
gtcaagtttt cgcagcttca ggagtatggc gtagaccggg tattcttgct tgaaaatgga     900
aatgtcgact cttctcagcg caatgtggta tttctagcgt acgccgaaaa gatccgccag     960
gtgcgggcag tggcaggtat gtcatgatct ttatccacct ttgatttaca tacccaaatg    1020
actgtaaatg cgaaggctcc ttgctatcgc gcttgctggg agcattaaag ttacgcagac    1080
```

```
ttcttctcca ctctgcgtaa tcagtcaagc tccctatatt gaaacttcgt ttagcagctt    1140
atccctaagg ctttctttct ctgcctcgta tgactgaatg ccatcagaat aagctgacaa    1200
gttttacaga gcagatccaa aggcttcaac gcaacagcag tatagaccat gaattttcca    1260
tcttttgggt tccaagacgg accctcgtaa gcaataacat cctagagagc gcaggcatca    1320
ttggagatgt gagcatcgct gagctgcctc tttactttt tcctctagag caggacgttc    1380
tttctttgga actggatgac tcttttgcgg acttgtacct ggtgagatct ttctcctgga    1440
gatagtgatc agtgctgatt cattttgtag cacaaggatc ctgggtgcat cttccattcc    1500
gcaaaggctc ttatggctat tcaacagaga catggctatt ttcctcggat agtaggcaaa    1560
ggcgatcatg ctcgacgact cgctgacctc ctgctgcgga tgaggaagga gattgacgca    1620
gaggaaagct caggactgac aggactgtct tccggggac ttttacccag ctcaagcatt    1680
gagagtttga tcatcattga ccgagaggtg gacttcggca cccctctgct tacacagcta    1740
acgtatgagg tctcatcga tgagttggta ggaatcaagc acaaccaagc ggacattgat    1800
acgacaattg caggggccag ctcaactccc caggcccagg agtcttccaa agcatctcaa    1860
caggctaagc aaggtcaaaa gcggaagatt cagttggatt cgtctgacca actgttcagt    1920
caactccgtg acgcgaattt tgctatagtc ggcgatatcc tgaataaggt agcacgtcga    1980
ttagaaacag attatgagag ccgtcataca gcaaaaacga caactgaact tcgcgagttt    2040
gtgaataaac taccatcata tcaactcgaa catcaaagct gagagttca caccaacctc    2100 gctgaggaaa tcatgaaaaa cacgcgctca gacactttcc gcaagatcct cgaagtgcaa    2160
cagaacgacg ctgcaggcgc cgacccaact taccaacatc ctctcattga ggaactcatc    2220
gcccgggata ttccactgaa gacaatcctc cgtttgcttt gtctcgaatc atgcatgtcc    2280
ggtggcctac ggcctaaaga cctcgagagt tttaaacgcc aagtcgtcca cgcatacggg    2340
caccaacacc tgctaacatt cagtgctttg gagaagatgg agcttctcca gccccggtcg    2400
tctgcaacca caatgctaat tcccggcacg ggcacccaaa cgggatcgaa acaaactac    2460 gcctactttc gcaaaaatct tcgcctggtc gtcgaagaag ttagcgagaa ggaacctgaa    2520
gatatcgctt atgtctacag cggtttcgcc cctctcagca ttcgccttgt gcagtgcgtc    2580
ttgcagaaat catacgtcat gtcgcttatg aaaggtggcc cggctgcgca cgcgaatacc    2640
gcatccccag gctggcttgg atatgaagat gtggtgaaga gtgcgcgtgg atcgacgttc    2700
agtattgtcc aaaagggcga cgataaagcg gttcgtgcgc ggcagacact gagtggtaac    2760
aatgcggcta agaccgtgta tgtgttcttc ctcggaggga tcacatttac ggaaatcgcg    2820
gcattgcggt tcattgcggc acaggaggcg ccgaggcgga acattgtgat ttgtactacg    2880
ggaatcatta atggagatcg gatgatggat gctgcgcttg agaagggggg gtttgccttg    2940
actgagtctt gacctcgtag agcgtacagt taatgtcata ggaactatac cgctatccat    3000
```

<210> SEQ ID NO 2
<211> LENGTH: 551
<212> TYPE: PRT
<213> ORGANISM: Aspergillus nidulans

<400> SEQUENCE: 2

```
His Glu Phe Ser Ile Phe Trp Val Pro Arg Arg Thr Leu Val Ser Asn
 1               5                  10                  15

Asn Ile Leu Glu Ser Ala Gly Ile Ile Gly Asp Val Ser Ile Ala Glu
            20                  25                  30
```

-continued

```
Leu Pro Leu Tyr Phe Phe Pro Leu Glu Gln Asp Val Leu Ser Leu Glu
        35                  40                  45

Leu Asp Asp Ser Phe Ala Asp Leu Tyr Leu His Lys Asp Pro Gly Cys
        50                  55                  60

Ile Phe His Ser Ala Lys Ala Leu Met Ala Ile Gln Gln Arg His Gly
 65                  70                  75                  80

Tyr Phe Pro Arg Ile Val Gly Lys Gly Asp His Ala Arg Arg Leu Ala
                85                  90                  95

Asp Leu Leu Arg Met Arg Lys Glu Ile Asp Ala Glu Glu Ser Ser
            100                 105                 110

Gly Leu Thr Gly Leu Ser Phe Arg Gly Leu Leu Pro Ser Ser Ser Ile
            115                 120                 125

Glu Ser Leu Ile Ile Ile Asp Arg Glu Val Asp Phe Gly Thr Pro Leu
        130                 135                 140

Leu Thr Gln Leu Thr Tyr Glu Gly Leu Ile Asp Glu Leu Val Gly Ile
145                 150                 155                 160

Lys His Asn Gln Ala Asp Ile Asp Thr Thr Ile Ala Gly Ala Ser Ser
                165                 170                 175

Thr Pro Gln Ala Gln Glu Ser Ser Lys Ala Ser Gln Gln Ala Lys Gln
            180                 185                 190

Gly Gln Lys Arg Lys Ile Gln Leu Asp Ser Ser Asp Gln Leu Phe Ser
            195                 200                 205

Gln Leu Arg Asp Ala Asn Phe Ala Ile Val Gly Asp Ile Leu Asn Lys
        210                 215                 220

Val Ala Arg Arg Leu Glu Thr Asp Tyr Glu Ser Arg His Thr Ala Lys
225                 230                 235                 240

Thr Thr Thr Glu Leu Arg Glu Phe Val Asn Lys Leu Pro Ser Tyr Gln
                245                 250                 255

Leu Glu His Gln Ser Leu Arg Val His Thr Asn Leu Ala Glu Glu Ile
            260                 265                 270

Met Lys Asn Thr Arg Ser Asp Thr Phe Arg Lys Ile Leu Glu Val Gln
        275                 280                 285

Gln Asn Asp Ala Ala Gly Ala Asp Pro Thr Tyr Gln His Pro Leu Ile
    290                 295                 300

Glu Glu Leu Ile Ala Arg Asp Ile Pro Leu Lys Thr Ile Leu Arg Leu
305                 310                 315                 320

Leu Cys Leu Glu Ser Cys Met Ser Gly Gly Leu Arg Pro Lys Asp Leu
                325                 330                 335

Glu Ser Phe Lys Arg Gln Val Val His Ala Tyr Gly His Gln His Leu
            340                 345                 350

Leu Thr Phe Ser Ala Leu Glu Lys Met Glu Leu Leu Gln Pro Arg Ser
        355                 360                 365

Ser Ala Thr Thr Met Leu Ile Pro Gly Thr Gly Thr Gln Thr Gly Ser
    370                 375                 380

Lys Thr Asn Tyr Ala Tyr Phe Arg Lys Asn Leu Arg Leu Val Val Glu
385                 390                 395                 400

Glu Val Ser Glu Lys Glu Pro Glu Asp Ile Ala Tyr Val Tyr Ser Gly
                405                 410                 415

Phe Ala Pro Leu Ser Ile Arg Leu Val Gln Cys Val Leu Gln Lys Ser
            420                 425                 430

Tyr Val Met Ser Leu Met Lys Gly Gly Pro Ala Ala His Ala Asn Thr
        435                 440                 445
```

```
Ala Ser Pro Gly Trp Leu Gly Tyr Glu Asp Val Val Lys Ser Ala Arg
    450                 455                 460
Gly Ser Thr Phe Ser Ile Val Gln Lys Gly Asp Asp Lys Ala Val Arg
465                 470                 475                 480
Ala Arg Gln Thr Leu Ser Gly Asn Asn Ala Ala Lys Thr Val Tyr Val
                485                 490                 495
Phe Phe Leu Gly Gly Ile Thr Phe Thr Glu Ile Ala Ala Leu Arg Phe
                500                 505                 510
Ile Ala Ala Gln Glu Ala Pro Arg Arg Asn Ile Val Ile Cys Thr Thr
            515                 520                 525
Gly Ile Ile Asn Gly Asp Arg Met Met Asp Ala Ala Leu Glu Lys Gly
    530                 535                 540
Gly Phe Ala Leu Thr Glu Ser
545                 550
```

<210> SEQ ID NO 3
<211> LENGTH: 430
<212> TYPE: PRT
<213> ORGANISM: Aspergillus fumigatus

<400> SEQUENCE: 3

```
His Glu Phe Ser Ile Phe Trp Leu Pro Arg Arg Thr Phe Val Ser Asn
  1               5                  10                  15
Lys Ile Leu Glu Asp Ala Gly Ile Ile Gly Asp Val Asn Ile Phe Glu
             20                  25                  30
Phe Pro Leu Tyr Phe Val Pro Leu Glu Gln Asp Val Leu Ser Leu Glu
         35                  40                  45
Leu Asp Asp Ser Phe Gly Asp Leu Tyr Leu His Lys Asp Pro Gly Cys
 50                  55                  60
Ile Phe Leu Ala Ala Lys Ala Leu Met Asp Ile Gln Gln Arg His Gly
65                  70                  75                  80
Tyr Phe Pro Arg Ile Ile Gly Lys Gly Asp His Ala Arg Arg Leu Ala
             85                  90                  95
Asp Leu Leu Leu Arg Met Arg Lys Glu Leu Asp Ala Glu Glu Ser Ser
            100                 105                 110
Gly Leu Arg Gly Pro Ser Ala Arg Gly Leu Leu Pro Ser Ala Ser Thr
        115                 120                 125
Glu Ser Leu Ile Ile Ile Asp Arg Met Val Asp Phe Gly Thr Pro Leu
130                 135                 140
Leu Thr Gln Leu Thr Tyr Glu Gly Leu Ile Asp Glu Phe Val Gly Ile
145                 150                 155                 160
Lys Asn Asn Gln Ala Asp Val Asp Thr Ala Ile Val Gly Ala Asn Ser
            165                 170                 175
Val Pro Gln Ala Gln Glu Ser Ser Lys Ala Pro Gln Thr Leu Lys
        180                 185                 190
Gln Gly Gln Lys Arg Lys Ile Gln Leu Asp Ser Ser Asp Gln Leu Phe
        195                 200                 205
Ser Gln Val Arg Asp Ala Asn Phe Ala Ile Val Gly Asp Ile Leu Asn
    210                 215                 220
Lys Val Ala Arg Arg Leu Glu Ser Glu Tyr Glu Thr Arg His Ala Ala
225                 230                 235                 240
Lys Thr Ala Ser Glu Leu Arg Glu Phe Val Asn Lys Leu Pro Ala Tyr
                245                 250                 255
Gln Leu Glu His Gln Ser Leu Arg Val His Thr Asn Leu Ala Gln Glu
            260                 265                 270
```

```
Ile Met Arg Asn Thr Arg Ser Asp Ile Phe Arg Lys Val Leu Glu Val
            275                 280                 285

Gln Gln Asn Asn Ala Ala Gly Thr Asp Pro Thr Tyr Gln His Asp Thr
        290                 295                 300

Ile Glu Glu Leu Ile Ala Arg Asp Val Pro Leu Lys Thr Val Leu Arg
305                 310                 315                 320

Leu Leu Cys Leu Glu Ser Cys Met Ser Gly Gly Leu Arg Ser Arg Asp
                325                 330                 335

Leu Glu Asn Phe Lys Lys Gln Ile Val His Ala Tyr Gly His Gln His
            340                 345                 350

Ile Leu Thr Phe Ser Ala Leu Glu Lys Met Glu Leu Leu Gln Pro Arg
            355                 360                 365

Ser Ser Ala Ala Thr Met Leu Ile Pro Thr Ala Gly Ala Gln Pro Gly
    370                 375                 380

Thr Lys Thr Asn Tyr Asn Tyr Leu Arg Lys Asn Leu Arg Leu Leu Val
385                 390                 395                 400

Glu Glu Val Ser Glu Glu Asp Pro Asn Asp Ile Ala Tyr Val Tyr Ser
                405                 410                 415

Ala Phe Ala Pro Leu Ser Ile Arg Leu Val Gln Cys Val Leu
            420                 425                 430

<210> SEQ ID NO 4
<211> LENGTH: 597
<212> TYPE: PRT
<213> ORGANISM: Rattus norvegicus

<400> SEQUENCE: 4

Met Ala Ala His Leu Ser Tyr Gly Arg Val Asn Leu Asn Val Leu Arg
1               5                   10                  15

Glu Ala Val Arg Arg Glu Leu Arg Glu Phe Leu Asp Lys Cys Ala Gly
            20                  25                  30

Ser Lys Ala Ile Val Trp Asp Glu Tyr Leu Thr Gly Pro Phe Gly Leu
        35                  40                  45

Ile Ala Gln Tyr Ser Leu Leu Lys Glu His Glu Val Glu Lys Met Phe
    50                  55                  60

Thr Leu Lys Gly Ser Arg Leu Pro Ala Ala Asp Val Lys Asn Ile Ile
65                  70                  75                  80

Phe Leu Val Arg Pro Arg Leu Glu Leu Met Asp Met Ile Ala Glu Asn
                85                  90                  95

Val Leu Ser Glu Asp Arg Arg Gly Pro Thr Arg Asp Phe His Ile Leu
            100                 105                 110

Phe Val Pro Arg Arg Ser Leu Leu Cys Glu Gln Arg Leu Lys Asp Leu
        115                 120                 125

Gly Val Leu Gly Ser Phe Ile Tyr Arg Glu Glu Tyr Ser Leu Asp Leu
    130                 135                 140

Ile Pro Phe Asp Gly Asp Leu Leu Ser Met Glu Ser Glu Ser Ala Phe
145                 150                 155                 160

Lys Glu Cys Tyr Leu Glu Gly Asp Gln Thr Ser Leu Tyr His Ala Ala
                165                 170                 175

Lys Gly Leu Met Thr Leu Gln Ala Leu Tyr Gly Thr Ile Pro Gln Ile
            180                 185                 190

Phe Gly His Gly Glu Cys Ala Arg Gln Val Ala Asn Met Met Val Arg
        195                 200                 205

Met Lys Arg Glu Phe Thr Gly Ser Gln Asn Ser Val Phe Pro Val Phe
    210                 215                 220
```

```
Asp Asn Leu Leu Leu Leu Asp Arg Asn Val Asp Leu Thr Pro Leu
225                 230                 235                 240

Ala Ser Gln Leu Thr Tyr Glu Gly Leu Ile Asp Glu Ile Tyr Gly Ile
            245                 250                 255

Gln Asn Ser Tyr Val Lys Leu Pro Pro Glu Lys Phe Ala Pro Lys Lys
            260                 265                 270

Gln Gly Gly Gly Gly Lys Asp Leu Pro Thr Glu Ala Lys Lys Leu
    275                 280                 285

Gln Leu Asn Ser Ala Glu Glu Leu Tyr Ala Glu Ile Arg Asp Lys Asn
    290                 295                 300

Phe Asn Ala Val Gly Ser Val Leu Ser Lys Lys Ala Lys Ile Ile Ser
305                 310                 315                 320

Ala Ala Phe Glu Glu Arg His Asn Ala Lys Thr Val Gly Glu Ile Lys
                325                 330                 335

Gln Phe Val Ser Gln Leu Pro His Met Gln Ala Ala Arg Gly Ser Leu
                340                 345                 350

Ala Asn His Thr Ser Ile Ala Glu Leu Ile Lys Asp Val Thr Thr Ser
            355                 360                 365

Glu Asp Phe Phe Asp Lys Leu Thr Val Glu Gln Glu Phe Met Ser Gly
370                 375                 380

Ile Asp Thr Asp Lys Val Asn Asn Tyr Ile Glu Asp Cys Ile Ala Gln
385                 390                 395                 400

Lys His Pro Leu Ile Lys Val Leu Arg Leu Val Cys Leu Gln Ser Met
                405                 410                 415

Cys Asn Ser Gly Leu Lys Gln Lys Val Leu Asp Tyr Tyr Lys Arg Glu
                420                 425                 430

Ile Leu Gln Thr Tyr Gly Tyr Glu His Ile Leu Thr Leu Asn Asn Leu
            435                 440                 445

Glu Lys Ala Gly Leu Leu Lys Ala Gln Thr Gly Gly Arg Asn Asn Tyr
450                 455                 460

Pro Thr Ile Arg Lys Thr Leu Arg Leu Trp Met Asp Asp Val Asn Glu
465                 470                 475                 480

Gln Asn Pro Thr Asp Ile Ser Tyr Val Tyr Ser Gly Tyr Ala Pro Leu
                485                 490                 495

Ser Val Arg Leu Ala Gln Leu Leu Ser Arg Pro Gly Trp Arg Ser Ile
            500                 505                 510

Glu Glu Val Leu Arg Ile Leu Pro Gly Pro His Phe Glu Glu Arg Gln
            515                 520                 525

Pro Leu Pro Thr Gly Val Gln Lys Lys Arg Gln Pro Gly Glu Asn Arg
    530                 535                 540

Val Thr Leu Val Phe Phe Leu Gly Gly Val Thr Phe Ala Glu Ile Ala
545                 550                 555                 560

Ala Leu Arg Phe Leu Ser Gln Leu Glu Asp Gly Gly Thr Glu Tyr Val
            565                 570                 575

Ile Ala Thr Thr Lys Leu Ile Asn Gly Ser Ser Trp Leu Glu Ala Leu
            580                 585                 590

Met Glu Lys Pro Phe
        595

<210> SEQ ID NO 5
<211> LENGTH: 691
<212> TYPE: PRT
<213> ORGANISM: Saccharomyces cerevisiae
```

<400> SEQUENCE: 5

```
Met Asn Arg Phe Trp Asn Thr Lys Lys Phe Ser Leu Thr Asn Ala Asp
 1               5                  10                  15
Gly Leu Cys Ala Thr Leu Asn Glu Ile Ser Gln Asn Asp Glu Val Leu
             20                  25                  30
Val Val Gln Pro Ser Val Leu Pro Val Leu Asn Ser Leu Leu Thr Phe
         35                  40                  45
Gln Asp Leu Thr Gln Ser Thr Pro Val Arg Lys Ile Thr Leu Leu Asp
     50                  55                  60
Asp Gln Leu Ser Asp Asp Leu Pro Ser Ala Leu Gly Ser Val Pro Gln
 65                  70                  75                  80
Met Asp Leu Ile Phe Leu Ile Asp Val Arg Thr Ser Leu Arg Leu Pro
                 85                  90                  95
Pro Gln Leu Leu Asp Ala Ala Gln Lys His Asn Leu Ser Ser Leu His
            100                 105                 110
Ile Ile Tyr Cys Arg Trp Lys Pro Ser Phe Gln Asn Thr Leu Glu Asp
        115                 120                 125
Thr Glu Gln Trp Gln Lys Asp Gly Phe Asp Leu Asn Ser Lys Lys Thr
    130                 135                 140
His Phe Pro Asn Val Ile Glu Ser Gln Leu Lys Glu Leu Ser Asn Glu
145                 150                 155                 160
Tyr Thr Leu Tyr Pro Trp Asp Leu Leu Pro Phe Pro Gln Ile Asp Glu
                165                 170                 175
Asn Val Leu Leu Thr His Ser Leu Tyr Asn Met Glu Asn Val Asn Met
            180                 185                 190
Tyr Tyr Pro Asn Leu Arg Ser Leu Gln Ser Ala Thr Glu Ser Ile Leu
        195                 200                 205
Val Asp Asp Met Val Asn Ser Leu Gln Ser Leu Ile Phe Glu Thr Asn
    210                 215                 220
Ser Ile Ile Thr Asn Val Val Ser Ile Gly Asn Leu Ser Lys Arg Cys
225                 230                 235                 240
Ser His Leu Leu Lys Lys Arg Ile Asp Glu His Gln Thr Glu Asn Asp
                245                 250                 255
Leu Phe Ile Lys Gly Thr Leu Tyr Gly Glu Arg Thr Asn Cys Gly Leu
            260                 265                 270
Glu Met Asp Leu Ile Ile Leu Glu Arg Asn Thr Asp Pro Ile Thr Pro
        275                 280                 285
Leu Leu Thr Gln Leu Thr Tyr Ala Gly Ile Leu Asp Asp Leu Tyr Glu
    290                 295                 300
Phe Asn Ser Gly Ile Lys Ile Lys Glu Lys Asp Met Asn Phe Asn Tyr
305                 310                 315                 320
Lys Glu Asp Lys Ile Trp Asn Asp Leu Lys Phe Leu Asn Phe Gly Ser
                325                 330                 335
Ile Gly Pro Gln Leu Asn Lys Leu Ala Lys Glu Leu Gln Thr Gln Tyr
            340                 345                 350
Asp Thr Arg His Lys Ala Glu Ser Val His Glu Ile Lys Glu Phe Val
        355                 360                 365
Asp Ser Leu Gly Ser Leu Gln Gln Arg Gln Ala Phe Leu Lys Asn His
    370                 375                 380
Thr Thr Leu Ser Ser Asp Val Leu Lys Val Val Glu Thr Glu Glu Tyr
385                 390                 395                 400
Gly Ser Phe Asn Lys Ile Leu Glu Leu Glu Leu Glu Ile Leu Met Gly
                405                 410                 415
```

```
Asn Thr Leu Asn Asn Asp Ile Glu Asp Ile Ile Leu Glu Leu Gln Tyr
            420                 425                 430

Gln Tyr Glu Val Asp Gln Lys Lys Ile Leu Arg Leu Ile Cys Leu Leu
        435                 440                 445

Ser Leu Cys Lys Asn Ser Leu Arg Glu Lys Asp Tyr Glu Tyr Leu Arg
    450                 455                 460

Thr Phe Met Ile Asp Ser Trp Gly Ile Glu Lys Cys Phe Gln Leu Glu
465                 470                 475                 480

Ser Leu Ala Glu Leu Gly Phe Phe Thr Ser Lys Thr Gly Lys Thr Asp
                485                 490                 495

Leu His Ile Thr Thr Ser Lys Ser Thr Arg Leu Gln Lys Glu Tyr Arg
            500                 505                 510

Tyr Ile Ser Gln Trp Phe Asn Thr Val Pro Ile Glu Asp Glu His Ala
        515                 520                 525

Ala Asp Lys Ile Thr Asn Glu Asn Asp Asp Phe Ser Glu Ala Thr Phe
    530                 535                 540

Ala Tyr Ser Gly Val Val Pro Leu Thr Met Arg Leu Val Gln Met Leu
545                 550                 555                 560

Tyr Asp Arg Ser Ile Leu Phe His Asn Tyr Ser Ser Gln Gln Pro Phe
                565                 570                 575

Ile Leu Ser Arg Glu Pro Arg Val Ser Gln Thr Glu Asp Leu Ile Glu
            580                 585                 590

Gln Leu Tyr Gly Asp Ser His Ala Ile Glu Glu Ser Ile Trp Val Pro
        595                 600                 605

Gly Thr Ile Thr Lys Lys Ile Asn Ala Ser Ile Lys Ser Asn Asn Arg
    610                 615                 620

Arg Ser Ile Asp Gly Ser Asn Gly Thr Phe His Ala Ala Glu Asp Ile
625                 630                 635                 640

Ala Leu Val Val Phe Leu Gly Gly Val Thr Met Gly Glu Ile Ala Ile
                645                 650                 655

Met Lys His Leu Gln Lys Ile Leu Gly Lys Gly Ile Asn Lys Arg
            660                 665                 670

Phe Ile Ile Ile Ala Asp Gly Leu Ile Asn Gly Thr Arg Ile Met Asn
        675                 680                 685

Ser Ile Ser
    690

<210> SEQ ID NO 6
<211> LENGTH: 575
<212> TYPE: PRT
<213> ORGANISM: Caenorhabditis elegans

<400> SEQUENCE: 6

Met Ala Ala Asn Glu Asp Arg Asp Ala Ala Ile Leu Asn Trp
  1             5                  10                  15

Glu Gly Thr Ser Glu Ile Lys Ser Ala Asn Glu Tyr Ser Arg Asn Leu
             20                  25                  30

Leu Phe Ser Val Leu Asp Ser Leu Asp Gly Asn Lys Thr Ile Val Trp
         35                  40                  45

Asp Arg Asp Arg Ser Val Met His Arg Val Asn Leu Phe Ala Gly Ala
     50                  55                  60

Ser Val Leu Ala Ala His Gly Val Val Ala Asn His Ser Ile Glu Thr
 65                  70                  75                  80

Lys Lys Ser Ala Ser Thr Pro His Val Val Phe Phe Leu Ala Pro Thr
                 85                  90                  95
```

-continued

```
Met Val Ser Leu Asp Leu Leu Cys Asp Tyr Ile Asp Asn Val Arg Asn
            100                 105                 110

Asp Ser Tyr Trp Glu Arg Leu Glu Ser Val Lys Glu Ile Pro Leu Cys
            115                 120                 125

Trp Leu Pro Arg Asp Gly Glu Cys Leu Ser Leu Ser Ser Pro Gln Ile
            130                 135                 140

Ala Ala Arg Leu Leu Ile Asn Gly Asp Trp Thr His Leu His Lys Cys
145                 150                 155                 160

Ala Val Ala Leu Asn Gln Leu Ile Asp Met Cys Arg Gly Arg Ser Ser
                165                 170                 175

Ser Ser Asn Gln Arg Pro Met Ser Ile Tyr Ala Lys Gly Lys Trp Ala
            180                 185                 190

Ser Asp Val Ala Lys Met Met Gly Lys Ile Arg Asn Ser Ala Glu Ala
            195                 200                 205

Asp Ser Met Thr Lys Asn Leu Asp Pro Ile Glu Gly Leu Leu Lys Ile
            210                 215                 220

Asn Arg Ile Val Leu Ile Asp Arg Trp Met Asp Pro Leu Thr Pro Met
225                 230                 235                 240

Leu Ser Gln Leu Thr Phe Tyr Gly Leu Leu Asp Glu Ile Tyr Gly Ile
                245                 250                 255

Gly Met Val Asn Ser Val Lys Val Pro Glu Met Glu Phe Lys Asn Glu
            260                 265                 270

Lys Asp Gly Asp Pro Phe Gln Glu Lys Glu Val Tyr Leu Ile Asp Glu
            275                 280                 285

Val Tyr His Arg Leu Lys His Ser His Ile Asn Ala Val Ser Ile Glu
            290                 295                 300

Ala Ser Lys Val Leu Ala Glu Ile Arg Asp Asp Glu Gln Phe Asp Arg
305                 310                 315                 320

Asp Lys Met Ser Val Ala Glu Tyr Ser Val Leu Val Lys Lys Met Pro
                325                 330                 335

Lys Ile Ile Asn Arg Lys Lys Met Ile Glu Val His Met Arg Leu Ala
            340                 345                 350

Glu Met Ile Gln Ser His Val Tyr Cys Lys Gln Ser Asp Ser Ile Lys
            355                 360                 365

Leu Glu Arg Asp Leu Leu Glu Tyr Ser Asp Ser Asp Lys Ala Ile Pro
            370                 375                 380

Leu Ile Glu Asp Leu Ile Phe Asp Ala Ser Pro Leu Asn Ala Val Leu
385                 390                 395                 400

Arg Leu Ile Ser Val His Ser Leu Thr Cys Gly Gly Leu Lys Pro Ser
                405                 410                 415

Val Leu Gln His Tyr Arg Arg Ile Val Asn Gln Ser Tyr Gly Ser Ser
            420                 425                 430

Ala Leu Asn Lys Val Leu Lys Met Gln Lys Met Gly Leu Ile Arg Glu
            435                 440                 445

Lys Gly Gly Gly Lys Met Gln Cys Glu Tyr Ala Gln Met Met Phe
            450                 455                 460

Gln Gln Met Lys Lys Asn His Asp Met Leu Pro Glu Glu Phe Ser Glu
465                 470                 475                 480

Ala Lys Leu Asp Asp Met Ala Tyr Ala Tyr Ser Gly Phe Ser Pro Leu
                485                 490                 495

Leu Cys Lys Met Leu Glu Glu Gly Asp Arg Val Lys Trp Val Gly Trp
            500                 505                 510
```

```
Pro Lys Thr Val Ile Gly Asp Lys Ser Asp Leu Ile Ala Glu Arg Asp
        515                 520                 525

Gly Arg Gly Thr Cys Val Phe Val Ile Gly Gly Leu Thr Arg Ser Glu
        530                 535                 540

Leu Ala Ile Ile Arg Glu Asn Leu Pro Asn Val Ala Leu Ile Thr Thr
545                 550                 555                 560

Ser Ala Leu Ile Thr Gly Asp Lys Leu Leu Asn Asn Ile Thr Asn
        565                 570                 575

<210> SEQ ID NO 7
<211> LENGTH: 6758
<212> TYPE: DNA
<213> ORGANISM: Aspergillus nidulans
<220> FEATURE:
<221> NAME/KEY: misc_feature
<222> LOCATION: (1)...(6758)
<223> OTHER INFORMATION: n = A,T,C or G

<400> SEQUENCE: 7
```

| | | | | | |
|---|---|---|---|---|---|
| tttttngggg | gnncccgaa | accnaaattt | tttttttta | aaaaanccc | ncaaagggc | 60 |
| ccaanaaaaa | aaaattttt | taaaaaaaaa | anccggatc | ccngggccaa | aattttggtt | 120 |
| caaaggggnc | ccaccccnt | ncaaaaccc | cggncgggaa | antttnttta | ttncgggcaa | 180 |
| agggaaccg | gaatgaaaaa | attngtccaa | agggtccaaa | gggcaatttt | ccccnttn | 240 |
| ccccaaaaaa | aaccggggtt | gnncaangng | ttttttnca | aaaaaaaa | anttgggngg | 300 |
| gnaagnngtt | aaaaaantg | gtattttccc | ttaangtaaa | ngttttgggt | ttggccccnt | 360 |
| ttccattttc | cctttgggng | ggttggnctc | aaggggtcc | cccaanccaa | aaacctgttt | 420 |
| ggtacattt | taaggccttg | tgccaagttn | gcanggtccc | tcgactttcg | gtgaanagga | 480 |
| atcggtctcg | gttaaaatan | aattcccaag | cttccttgat | aatgtgggtt | ttgattgttg | 540 |
| attcatttga | nanagcgtgt | ttgnatttc | gcttgtgttt | tcgaaattca | tatagnactt | 600 |
| ggtgtgatag | ggcgggtctt | tcgttcttga | tacccaggat | agtgagacta | cccaaggatt | 660 |
| cactatttct | tcttcttcgg | acacctttca | ctggcttggt | gtatctactc | ccatgtagca | 720 |
| gcaggcggct | catgcatcgt | catcaaccac | ttcctctccg | tagttctctt | cctccttggc | 780 |
| ttcattctct | gacaattggc | ggccctgggc | ttcagctgtt | ttcttgtcca | cctccatacg | 840 |
| ttcggtcaaa | aacaaattga | tgtcattctg | tagcgcggga | accagttttc | gaagctccga | 900 |
| gagataggtg | actttgactt | ttatgttttc | ctctgagggg | cttggtgcgg | gtgagttgat | 960 |
| ggtgtgctcg | aacgtgcggt | tcagctgagg | cgaggtgtat | tgggcctgga | gccgatacga | 1020 |
| ctgagatgag | gatgtcgacg | ccattctgaa | tatctgctag | cctgttgttc | ttgaagctgc | 1080 |
| tattcaggag | gggaaaagag | gaaagaggga | gaaattgatg | gcggggcgag | ctagcagcgg | 1140 |
| gagtcagtcc | agtgttgcgg | agcagacaaa | cgatcgacag | gaataccaa | cgatcgcctg | 1200 |
| gccggctggt | cttctaggct | actgtgttaa | tctctctgga | atagattcga | atcatcagat | 1260 |
| ccaaatcagt | caacatgaca | atgtctgcat | agtgaagaat | gaactccttg | ctgtcttgat | 1320 |
| tacatactca | gccccgaacc | tccaccggca | ctgcccgctg | ctggaaatgc | tgcgctcccc | 1380 |
| cgtcaccgtc | tctccagagc | gctcagcctc | tcgaccaccg | ctccctcgtt | cctcttctga | 1440 |
| cttcgatgac | gacccagacc | gtccaggctc | ctccggaagt | gatgcctcgt | cggtgatctc | 1500 |
| aaatgcgact | gcattccaaa | ccacccctca | tcgccgcgac | cgcgaccgcg | accgcgaacc | 1560 |
| ggatccgtcc | tactcccctc | gtaccgttct | tcggacacca | cccaccgaaa | cttcagccgc | 1620 |
| agcctcagcc | tcagcgcaag | gcccagggca | tccccgact | tcattcatgc | cgcatcatga | 1680 |

```
tcctacgagc agaaagccgt ctggacgagt ctacccgtcg gacctgcaca agcgctcgcg   1740
gcaccactcg cagggttct tcgagccgtc cctgcccacg gcttcgtcat ctgacgcgac   1800
gctttcagcg tctaggatag cagctcaggc tggtatgcaa agccagggtc agcattcgtc   1860
ttctacgatc cctcaggttc ctccgaaacg ggctgtgcag ggacatggtt cagacaacgg   1920
gtcaggatcg gtctcaccac ctcccccgat tccggcttcc cagccgcaga gacccgggtc   1980
tgcaggctcg ccatatcaga actcgaatgc cactaccgga gggcatggtg tagggcaggc   2040
tgcggcgacg acggctgcca accatgtctt tccacggcta ccgccgccgg gagtggaagc   2100
acatcctaat gagcgagaac ataagaagac tgagaaggaa aagtcgaaaa tgaagctttt   2160
ttcgaagccg aagcatattg gcatcagtcg tgataaggac tttaaggaca ggggactccc   2220
gtcaccgaac aagatttccg ggctgacacg gatagtcagt gcgtctgcga cgaatcttgc   2280
ggatatctat ccgtcgaata actcgtctat gtatagcctg tcgaatgcat cggcgagcac   2340
tgttgtaccg gctgataagc cttcggtacc tgagaaagag aaagacaagg aaaaggacaa   2400
agaaaaggac aaggaaaagg cccaccggca tcatcatttc ttgtcgcggc agaagctgaa   2460
gctgaaggat ttgaaagata agatgatcat ttacaacctg ccgctctctt ctgcggcgag   2520
taactccaga ccgtcagacc ctaatgctcc gcagtcacta tactctttca ctccggcttc   2580
cccgagtgct actactactt cttttcagcaa gtctgtaggc gggttggatc tattacatgg   2640
tgggcgagcg ctccgcgaca agaagaagga agagaagacg cttgcagaag aacagccgga   2700
atggttggcg aattcgacag tcgctggggc agctactgca gggtttgctg ggccgtcatc   2760
gttaggaagt actgggggct tcctcactga ggctgttgta cgggaaacgt tacaaggctt   2820
tggtcttcat aatatgagtc ctgaagatgc atgggacttc ttaaaagcaa aactgttggt   2880
gattttcgac ggcgaagatg ttcgcattgc aattgaggat ctgaacaaac tagtgatcat   2940
ccatattcag cgctgcgtgc agaggcgtac gccgacagct atagtcgacg atctacgcgg   3000
gctgctggaa gctggctttg ccaccttgaa ccatacccct aacggcgtac cggatgataa   3060
gctggtgccc catctcgtgc agatctggat gctagtattt ggcaccattc tccctttcat   3120
tcaagccgtc ttcctacccc tagatcttga attcaaaggc tgtggctccg tcatgaacat   3180
acgagaagca aagaacttct ggagcctcgc gctagatggg gaatatcccg gttgcgagct   3240
cgaagtccgc aacctcgttc ttatcgcctt ccgcgacatg gtcatcatca accgctacga   3300
taacctcaaa gccaccttct cccgcttgag ccttgacagc atcaagctcg gcaactccgc   3360
ccttagcgta acaacgaaaa gcagtaataa tagcaataac ggccgcccta cgacctccgc   3420
atccttcgac ggcgggtttg gcagttacag ttcccaatca tccaccttcc taaatacagc   3480
cggcagcttt tcttcggaat ccccaggata caaccgcagt cgtgctacct ccaacaccctc   3540
ctcaaaccc gaccaactca tcttccaatc cttctcttcc ccttctcaac ggcccacgat   3600
tatccaccgc gcaaacaacg catcagatac atctcacgtc atcaccgaga cagtcggccg   3660
catgctccag tgcatgagtg tcctcgcaag tgtgcagacc aacgatactg cgcaggaacg   3720
aattgagaca ctcagcaaag atctcaagca taactggttg gacgcggcc ggacaggaag   3780
agataggcgt ggttttgtgg ggacgaagat tcgcccgccg atcgttgcac aggcgagcga   3840
taactctact gattctaata tggacgagtt gagttccaag aggttgcagc aggagttgag   3900
tgttttgtga tgtgaagata tcgatatctt ctcttcgtag attggttcac tctatagcac   3960
ttcgttgttt gtctggtaca aagcaaggat tatgtgtctc agcgcggact tttatctatc   4020
ctcttatctc catttattgt tctgggttgg tgcagtgggt tcgtgggttt tggattgagt   4080
```

```
tctgctggcg ttcaataggg ctacatagga cgcaatacta caaaaatcaa gtgaatcgcg    4140
cgtcaaagca ttcatatctg ctctccctgt tcgagctagt gacaagttcc agaaaccacc    4200
tcgccggcag ctctaagtcc aacctactct gtgtttgtat tcatccacag atcatcaaat    4260
aagtcaatct tacaccctca gatgttaatg tcatccgggt ttccggatca tgataacgcc    4320
aaagacttca gccaatcttt tcagggcatc caaataagcg aaatgaaata cacgatagga    4380
acgaagacaa actcctagat aaactgcatg caggtagaat ctcttcgctc cgatctactc    4440
cttagtatca tcagtcccaa aagctgcttc atgagcagat gtagcagcgt tcttgctcaa    4500
ttccttgaac ttcttctgga gcacggcaat aggatacttc tccccgccgt cgctctgaat    4560
cgcctccatg atacgatgcc acttttcctg ctcgaatttg tcctcaatct ccttttttcaa    4620
ccggagaaga cgtgcttcct gcggccagtt agtgttgatg tcagcaatca ggctattgct    4680
atccggggtg tggtgtgatt cagggtagcc agacatacat cttcgatcgt gatccccaca    4740
aaattcgcct tcatagtact ccagcgtaat ctaagtgtcg tactaccgac cttgatcccc    4800
gttttctcag tgaagagcct gttgatctgc gtccatggct gcttttcctc gtcgcgcagg    4860
tgtaggatca tacggtccat ttcacccgct gttgcaaggc tggttgggat gggggggaaga    4920
gttgcgcggg ctggtgctcc ttccggtgta ccagtgccat ttccggcgac aaccccggta    4980
tccttcttgg atttcttaga aggggttttg gggaggcgc gcttgccagt gcgcttgccg    5040
agtttagggg tttcttttttt ggtcatcgac actggcgagg cgttggtgtt ctggaaatta    5100
ttcgttaact ccgctttgtg tttgtacagt agcggatatg gttactgact tacgtttttcc    5160
tcatcttctg cttcgatgcc ggatagaggc tgctcatccc cgttgtcgtt cgcttcattc    5220
atcgctgcat tggcaacttc ccgtccgtgg tcggtgcgga tatttatggg ggtgaactca    5280
atggaatggg tggatagttc tgtactgatg tcgaagtcca tacttgaggt gatgagaagc    5340
tgatatcttc ttgtcgtgga cgttaatagc tagtttcgac taaggtatga gaagctcgag    5400
ggttgagtga agatgagcga gcggatacag aaacccaggc ttgactgact acaagcttga    5460
atgagaaatc agggaagtga attgaatgac tagatggagg tcacggtttg gtgtgagggc    5520
tagagatgaa cttgagttgg tgcaggaaga tgaacgagca ggatgtagga gggtagaaaa    5580
atggcagtat gattcctcac ttggagaaga ggaagagtac accatgaagt caagaagtgt    5640
tgctcctagt tgaggtgaaa cgctgggaag agcgaggaga cttcgtttgt gttggtgata    5700
ttgagtgagc atcatcagga gctgcttctt ggacatgccg cttatgttta cgaaataaag    5760
agataaatat actttaatga tagactcaga ctctggtaca tactccacgg atttggtaac    5820
attgaaacta tactgaactt cattcgcgtg ccatgattgt cattcgattc caggtccata    5880
agacgaagga ttgctagtag gctacaggaa ctagtcataa tagcagcggt ctgggctctg    5940
gttacaaaga ctaatgcgtt atttatacaa tacagatctc tggccatgga actacgctgc    6000
actgctatca gcttgctcca tgtcttggga aacataccct aaaggctctg ctgagtgta    6060
agcgcggtac taacgcctta ttaatgctct atactccaac cagcatgatt ggcactgaca    6120
agatgctgac ggtgaattag caaagcatga aagcttgctt gcttcttcgt atacagtttg    6180
ctgtttgatg attcgattct cgactaaaaa agtgaagcgg catccttcag ctctcgcccg    6240
agttgcgatt cattaatcgc acgattgatt cggatgctca gttgttgtgt cacatggttg    6300
aagataatca ctgatcctca tctcgatcaa ctccatcgcc ggctggacca aactgctcaa    6360
tcggtttctg aggtcagtgg gactgaccgt tgagacgatc gatttgtccg agccaacaca    6420
catcgtgacc tgaaatatcc caccttggta gttacactaa agggctcggc agcgctcagt    6480
```

-continued

```
ccatagactg acaagaaagc attgggaaga agtacctgca ctaaccctga gaactgacaa    6540
ctctgcatgc aaaccgggca acgccattcg ccagctgtgc tccatcgtcc ttagctgcag    6600
tttcttctgg gaacttcgcg atccgcggcc gggggatcca ctagttctag agcggccgcc    6660
accgcggtgg agctccagct tttgttccct ttagtgaggg ttaatttcga gcttggcgta    6720
atcatggtca gctgtttc ctgtgtgaaa ttgttatc                              6758
```

<210> SEQ ID NO 8
<211> LENGTH: 847
<212> TYPE: PRT
<213> ORGANISM: Aspergillus nidulans

<400> SEQUENCE: 8

```
Met Leu Arg Ser Pro Val Thr Val Ser Pro Glu Arg Ser Ala Ser Arg
  1               5                  10                  15

Pro Pro Leu Pro Arg Ser Ser Asp Phe Asp Asp Pro Asp Arg
             20                  25                  30

Pro Gly Ser Ser Gly Ser Asp Ala Ser Ser Val Ile Ser Asn Ala Thr
             35                  40                  45

Ala Phe Gln Thr Thr Pro His Arg Arg Asp Arg Asp Arg Asp Arg Glu
 50                  55                  60

Pro Asp Pro Ser Tyr Ser Pro Arg Thr Val Leu Arg Thr Pro Pro Thr
 65                  70                  75                  80

Glu Thr Ser Ala Ala Ala Ser Ala Ser Ala Gln Gly Pro Gly His Pro
                 85                  90                  95

Pro Thr Ser Phe Met Pro His His Asp Pro Thr Ser Arg Lys Pro Ser
            100                 105                 110

Gly Arg Val Tyr Pro Ser Asp Leu His Lys Arg Ser Arg His His Ser
            115                 120                 125

Gln Gly Phe Phe Glu Pro Ser Leu Pro Thr Ala Ser Ser Ser Asp Ala
130                 135                 140

Thr Leu Ser Ala Ser Arg Ile Ala Ala Gln Ala Gly Met Gln Ser Gln
145                 150                 155                 160

Gly Gln His Ser Ser Thr Ile Pro Gln Val Pro Pro Lys Arg Ala
            165                 170                 175

Val Gln Gly His Gly Ser Asp Asn Gly Ser Gly Ser Val Ser Pro Pro
            180                 185                 190

Pro Pro Ile Pro Ala Ser Gln Pro Gln Arg Pro Gly Ser Ala Gly Ser
            195                 200                 205

Pro Tyr Gln Asn Ser Asn Ala Thr Thr Gly Gly His Gly Val Gly Gln
            210                 215                 220

Ala Ala Ala Thr Thr Ala Ala Asn His Val Phe Pro Arg Leu Pro Pro
225                 230                 235                 240

Pro Gly Val Glu Ala His Pro Asn Glu Arg Glu His Lys Lys Thr Glu
            245                 250                 255

Lys Glu Lys Ser Lys Met Lys Leu Phe Ser Lys Pro Lys His Ile Gly
            260                 265                 270

Ile Ser Arg Asp Lys Asp Phe Lys Asp Arg Gly Leu Pro Ser Pro Asn
            275                 280                 285

Lys Ile Ser Gly Leu Thr Arg Ile Val Ser Ala Ser Ala Thr Asn Leu
            290                 295                 300

Ala Asp Ile Tyr Pro Ser Asn Asn Ser Ser Met Tyr Ser Leu Ser Asn
305                 310                 315                 320
```

```
Ala Ser Ala Ser Thr Val Val Pro Ala Asp Lys Pro Ser Val Pro Glu
            325                 330                 335
Lys Glu Lys Asp Lys Glu Lys Asp Lys Glu Lys Asp Lys Glu Lys Ala
            340                 345                 350
His Arg His His His Phe Leu Ser Arg Gln Lys Leu Lys Leu Lys Asp
            355                 360                 365
Leu Lys Asp Lys Asp Asp His Tyr Asn Leu Pro Leu Ser Ser Ala Ala
        370                 375                 380
Ser Asn Ser Arg Pro Ser Asp Pro Asn Ala Pro Gln Ser Leu Tyr Ser
385                 390                 395                 400
Phe Thr Pro Ala Ser Pro Ser Ala Thr Thr Ser Phe Ser Lys Ser
            405                 410                 415
Val Gly Gly Leu Asp Leu Leu His Gly Gly Arg Ala Leu Arg Asp Lys
            420                 425                 430
Lys Lys Glu Glu Lys Thr Leu Ala Glu Glu Gln Pro Glu Trp Leu Ala
            435                 440                 445
Asn Ser Thr Val Ala Gly Ala Ala Thr Ala Gly Phe Ala Gly Pro Ser
            450                 455                 460
Ser Leu Gly Ser Thr Gly Gly Phe Leu Thr Glu Ala Val Val Arg Glu
465                 470                 475                 480
Thr Leu Gln Gly Phe Gly Leu His Asn Met Ser Pro Glu Asp Ala Trp
            485                 490                 495
Asp Phe Leu Lys Ala Lys Leu Leu Val Ile Phe Asp Gly Glu Asp Val
            500                 505                 510
Arg Ile Ala Ile Glu Asp Leu Asn Lys Leu Val Ile His Ile Gln
            515                 520                 525
Arg Cys Val Gln Arg Arg Thr Pro Thr Ala Ile Val Asp Asp Leu Arg
            530                 535                 540
Gly Leu Leu Glu Ala Gly Phe Ala Thr Leu Asn His Thr Leu Asn Gly
545                 550                 555                 560
Val Pro Asp Asp Lys Leu Val Pro His Leu Val Gln Ile Trp Met Leu
            565                 570                 575
Val Phe Gly Thr Ile Leu Pro Phe Ile Gln Ala Val Phe Leu Pro Leu
            580                 585                 590
Asp Leu Glu Phe Lys Gly Cys Gly Ser Val Met Asn Ile Arg Glu Ala
            595                 600                 605
Lys Asn Phe Trp Ser Leu Ala Leu Asp Gly Glu Tyr Pro Gly Cys Glu
            610                 615                 620
Leu Glu Val Arg Asn Leu Val Leu Ile Ala Phe Arg Asp Met Val Ile
625                 630                 635                 640
Ile Asn Arg Tyr Asp Asn Leu Lys Ala Thr Phe Ser Arg Leu Ser Leu
            645                 650                 655
Asp Ser Ile Lys Leu Gly Asn Ser Ala Leu Ser Val Thr Thr Lys Ser
            660                 665                 670
Ser Asn Asn Ser Asn Asn Gly Arg Pro Thr Thr Ser Ala Ser Phe Asp
            675                 680                 685
Gly Gly Phe Gly Ser Tyr Ser Ser Gln Ser Ser Thr Phe Leu Asn Thr
            690                 695                 700
Ala Gly Ser Phe Ser Ser Glu Ser Pro Gly Tyr Asn Arg Ser Arg Ala
705                 710                 715                 720
Thr Ser Asn Thr Ser Ser Asn Pro Asp Gln Leu Ile Phe Gln Ser Phe
            725                 730                 735
```

```
Ser Ser Pro Ser Gln Arg Pro Thr Ile Ile His Arg Ala Asn Asn Ala
            740                 745                 750

Ser Asp Thr Ser His Val Ile Thr Glu Thr Val Gly Arg Met Leu Gln
            755                 760                 765

Cys Met Ser Val Leu Ala Ser Val Gln Thr Asn Asp Thr Ala Gln Glu
            770                 775                 780

Arg Ile Glu Thr Leu Ser Lys Asp Leu Lys His Asn Trp Leu Gly Arg
785                 790                 795                 800

Gly Arg Thr Gly Arg Asp Arg Gly Phe Val Gly Thr Lys Ile Arg
                805                 810                 815

Pro Pro Ile Val Ala Gln Ala Ser Asp Asn Ser Thr Asp Ser Asn Met
            820                 825                 830

Asp Glu Leu Ser Ser Lys Arg Leu Gln Gln Glu Leu Ser Val Leu
            835                 840                 845

<210> SEQ ID NO 9
<211> LENGTH: 847
<212> TYPE: PRT
<213> ORGANISM: Aspergillus nidulans

<400> SEQUENCE: 9

Met Leu Arg Ser Pro Val Thr Val Ser Pro Glu Arg Ser Ala Ser Arg
 1               5                  10                  15

Pro Pro Leu Pro Arg Ser Ser Asp Phe Asp Asp Pro Asp Arg
                20                  25                  30

Pro Gly Ser Ser Gly Ser Asp Ala Ser Ser Val Ile Ser Asn Ala Thr
            35                  40                  45

Ala Phe Gln Thr Thr Pro His Arg Arg Asp Arg Asp Arg Asp Arg Glu
 50                  55                  60

Pro Asp Pro Ser Tyr Ser Pro Arg Thr Val Leu Arg Thr Pro Pro Thr
65                  70                  75                  80

Glu Thr Ser Ala Ala Ala Ser Ala Ser Ala Gln Gly Pro Gly His Pro
                85                  90                  95

Pro Thr Ser Phe Met Pro His His Asp Pro Thr Ser Arg Lys Pro Ser
            100                 105                 110

Gly Arg Val Tyr Pro Ser Asp Leu His Lys Arg Ser Arg His His Ser
            115                 120                 125

Gln Gly Phe Phe Glu Pro Ser Leu Pro Thr Ala Ser Ser Ser Asp Ala
130                 135                 140

Thr Leu Ser Ala Ser Arg Ile Ala Ala Gln Ala Gly Met Gln Ser Gln
145                 150                 155                 160

Gly Gln His Ser Ser Thr Ile Pro Gln Val Pro Pro Lys Arg Ala
                165                 170                 175

Val Gln Gly His Gly Ser Asp Asn Gly Ser Gly Ser Val Ser Pro Pro
            180                 185                 190

Pro Pro Ile Pro Ala Ser Gln Pro Gln Arg Pro Gly Ser Ala Gly Ser
            195                 200                 205

Pro Tyr Gln Asn Ser Asn Ala Thr Thr Gly Gly His Gly Val Gly Gln
            210                 215                 220

Ala Ala Ala Thr Thr Ala Ala Asn His Val Phe Pro Arg Leu Pro Pro
225                 230                 235                 240

Pro Gly Val Glu Ala His Pro Asn Glu Arg Glu His Lys Lys Thr Glu
                245                 250                 255

Lys Glu Lys Ser Lys Met Lys Leu Phe Ser Lys Pro Lys His Ile Gly
            260                 265                 270
```

-continued

```
Ile Ser Arg Asp Lys Asp Phe Lys Asp Arg Gly Leu Pro Ser Pro Asn
        275                 280                 285

Lys Ile Ser Gly Leu Thr Arg Ile Val Ser Ala Ser Ala Thr Asn Leu
        290                 295                 300

Ala Asp Ile Tyr Pro Ser Asn Asn Ser Ser Met Tyr Ser Leu Ser Asn
305                 310                 315                 320

Ala Ser Ala Ser Thr Val Val Pro Ala Asp Lys Pro Trp Val Pro Glu
                325                 330                 335

Lys Glu Lys Asp Lys Glu Lys Asp Lys Glu Lys Asp Lys Glu Lys Ala
                340                 345                 350

His Arg His His His Phe Leu Ser Arg Gln Lys Leu Lys Leu Lys Asp
                355                 360                 365

Leu Lys Asp Lys Asp Asp His Tyr Asn Leu Pro Leu Ser Ser Ala Ala
        370                 375                 380

Ser Asn Ser Arg Pro Ser Asp Pro Asn Ala Pro Gln Ser Leu Tyr Ser
385                 390                 395                 400

Phe Thr Pro Ala Ser Pro Ser Ala Thr Thr Thr Ser Phe Ser Lys Ser
                405                 410                 415

Val Gly Gly Leu Asp Leu Leu His Gly Gly Arg Ala Leu Arg Asp Lys
                420                 425                 430

Lys Lys Glu Glu Lys Thr Leu Ala Glu Glu Gln Pro Glu Trp Leu Ala
        435                 440                 445

Asn Ser Thr Val Ala Gly Ala Ala Thr Ala Gly Phe Ala Gly Pro Ser
        450                 455                 460

Ser Leu Gly Ser Thr Gly Gly Phe Leu Thr Glu Ala Val Val Arg Glu
465                 470                 475                 480

Thr Leu Gln Gly Phe Gly Leu His Asn Met Ser Pro Glu Asp Ala Trp
                485                 490                 495

Asp Phe Leu Lys Ala Lys Leu Leu Val Ile Phe Asp Gly Glu Asp Val
                500                 505                 510

Arg Ile Ala Ile Glu Asp Leu Asn Lys Leu Val Ile Ile His Ile Gln
        515                 520                 525

Arg Cys Val Gln Arg Arg Thr Pro Thr Ala Ile Val Asp Asp Leu Arg
        530                 535                 540

Gly Leu Leu Glu Ala Gly Phe Ala Thr Leu Asn His Thr Leu Asn Gly
545                 550                 555                 560

Val Pro Asp Asp Lys Leu Val Pro His Leu Val Gln Ile Trp Met Leu
                565                 570                 575

Val Phe Gly Thr Ile Leu Pro Phe Ile Gln Ala Val Phe Leu Pro Leu
                580                 585                 590

Asp Leu Glu Phe Lys Gly Cys Gly Ser Val Met Asn Ile Arg Glu Ala
        595                 600                 605

Lys Asn Phe Trp Ser Leu Ala Leu Asp Gly Glu Tyr Pro Gly Cys Glu
        610                 615                 620

Leu Glu Val Arg Asn Leu Val Leu Ile Ala Phe Arg Asp Met Val Ile
625                 630                 635                 640

Ile Asn Arg Tyr Asp Asn Leu Lys Ala Thr Phe Ser Arg Leu Ser Leu
                645                 650                 655

Asp Ser Ile Lys Leu Gly Asn Ser Ala Leu Ser Val Thr Thr Lys Ser
                660                 665                 670

Ser Asn Asn Ser Asn Asn Gly Arg Pro Thr Thr Ser Ala Ser Phe Asp
                675                 680                 685
```

-continued

```
Gly Gly Phe Gly Ser Tyr Ser Gln Ser Ser Thr Phe Leu Asn Thr
    690             695             700

Ala Gly Ser Phe Ser Ser Glu Ser Pro Gly Tyr Asn Arg Ser Arg Ala
705             710             715             720

Thr Ser Asn Thr Ser Ser Asn Pro Asp Gln Leu Ile Phe Gln Ser Phe
            725             730             735

Ser Ser Pro Ser Gln Arg Pro Thr Ile Ile His Arg Ala Asn Asn Ala
        740             745             750

Ser Asp Thr Ser His Val Ile Thr Glu Thr Val Gly Arg Met Leu Gln
            755             760             765

Cys Met Ser Val Leu Ala Ser Val Gln Thr Asn Asp Thr Ala Gln Glu
770             775             780

Arg Ile Glu Thr Leu Ser Lys Asp Leu Lys His Asn Trp Leu Gly Arg
785             790             795             800

Gly Arg Thr Gly Arg Asp Arg Gly Phe Val Gly Thr Lys Ile Arg
            805             810             815

Pro Pro Ile Val Ala Gln Ala Ser Asp Asn Ser Thr Asp Ser Asn Met
            820             825             830

Asp Glu Leu Ser Ser Lys Arg Leu Gln Gln Glu Leu Ser Val Leu
            835             840             845

<210> SEQ ID NO 10
<211> LENGTH: 826
<212> TYPE: PRT
<213> ORGANISM: Aspergillus fumigatus

<400> SEQUENCE: 10

Met Met Leu Arg Ser Pro Ile Pro Pro Glu Arg Thr Ser Ser Arg Ser
1               5               10              15

Pro Ala Pro Pro Arg Pro Ser Phe Asp Asp Glu Leu Glu Arg Pro Gly
            20              25              30

Ser Ala Gly Ser Asp Ala Ser Ser Val Ala Ser Asn Val Thr Thr Val
        35              40              45

Ser Ala Ile Gln Ser Ser Leu Asn Asn Phe Gly Ala Ala Pro Asp Ala
    50              55              60

Ser Ser Pro Arg Ile Pro Arg Thr Ser Thr Asn Gly Ser Gly Thr
65              70              75              80

Thr Asp Asp Asn Pro Arg Arg Pro Ser Ala Ser Ser Leu Met Pro Gln
            85              90              95

Asn Glu Met Thr Ser Arg Lys Ile Ser Gly Arg Val Val Pro Pro Asp
            100             105             110

Leu Ser Arg His Arg Pro Arg His His Ser Gln Gly Phe Phe Glu Pro
        115             120             125

Ser Leu Pro Thr Ala Ser Leu Ser Asp Val Thr Leu Ser Ala Ser Arg
    130             135             140

Ile Ala Ala Gln Ala Ala Met Gln Gln Gln Ser Ser Ala Ala Gln His
145             150             155             160

Pro Pro Lys Arg Leu Pro Ser Asn Val Gln Gly Pro Asp Gly Arg Gly
            165             170             175

Gly Ser Ile Ser Pro Leu Pro Pro Gln Gln Val Leu Ala Ala
        180             185             190

Pro Gly Ser Gly Ser Thr Ser Gly Gln Ser Tyr Gln Asn Gly Ile Val
    195             200             205

Gly Gly Asn Ala Leu Ala Ala Thr Thr Ala Ala Asn Val Val Phe Pro
    210             215             220
```

-continued

```
Arg Gly Pro Ala Leu Gln Pro Gly Met Ala Ser Asp Gln Ala Gln Pro
225                 230                 235                 240

Glu Arg Glu Gln Lys Gln Lys Gly Asp Lys Pro Lys Met Lys Leu Phe
            245                 250                 255

Ser Lys Pro Lys His Ile Gly Ile Ser Arg Asp Lys Asp Ser Tyr Gly
        260                 265                 270

Lys Asp Lys Gly Ile Pro Ser Pro Ser Lys Met Gly Phe Pro Gly Ser
    275                 280                 285

Ser Gly Leu Ser Arg Ile Val Ser Gly Ser Thr Asp Thr Leu Pro Ser
290                 295                 300

Asn Asn Ser Ser Met Tyr Ser Leu Ser Asn Ala Ser Val Asn Thr Val
305                 310                 315                 320

Val Pro Ala Asp Arg Gln Ala Ser Ser Glu Lys Asp Lys Asp Lys Asp
            325                 330                 335

Lys Ala His Lys His His Phe Leu Ser Arg Gln Lys Leu Lys Leu Lys
        340                 345                 350

Asp Arg Asp Asp His Tyr Asn Leu Pro Leu Ser Ser Ala Ser Ser Asn
    355                 360                 365

Ser Lys Pro Ser Asp Pro Asn Ala Pro Gln Ser Leu Tyr Ser Phe Thr
370                 375                 380

Pro Ala Ser Pro Asn Ala Gly Ser Thr Thr Phe Ser Lys Thr Val Gly
385                 390                 395                 400

Gly Leu Asp Leu Leu His Gly Gly Arg Ala Leu Arg Glu Lys Lys Lys
            405                 410                 415

Glu Glu Lys Leu Arg Glu Glu Ile Glu Gln Asp Leu Val Val Ser Cys
        420                 425                 430

Ala Thr Pro Ala Val Phe Ser Gly Pro Ser Ser Leu Gly Asn Ser Thr
    435                 440                 445

Gly Leu Leu Pro Glu Ala Ala Leu Arg Glu Thr Leu Ser Gly Phe Gly
450                 455                 460

Leu His Asn Met Thr Pro Asp Asp Ala Trp Asp Phe Leu Lys Ala Lys
465                 470                 475                 480

Leu Leu Val Ile Phe Asp Gly Glu Asp Val Arg Ile Ala Ile Glu Asp
            485                 490                 495

Leu Asn Lys Leu Val Leu Ile His Ile Gln Arg Cys Val Gln Lys His
        500                 505                 510

Thr Pro Thr Ala Ile Val Asp Asp Leu Arg Glu Leu Leu Glu Thr Gly
    515                 520                 525

Cys Ala Ser Leu Asn His Thr Leu Asn Gly Val Pro Asp Glu Lys Leu
530                 535                 540

Val Pro His Leu Val Gln Ile Trp Leu Leu Val Phe Gly Thr Ile Leu
545                 550                 555                 560

Pro Phe Ile Gln Ala Val Phe Leu Pro Leu Asp Leu Glu Phe Arg Gly
            565                 570                 575

Ala Gly Ser Val Met Asn Leu Arg Glu Ala Lys Asp Phe Trp Asn Ser
        580                 585                 590

Val Pro Thr Gly Lys Asp Phe Glu Asn Glu Leu Glu Val Arg His Leu
    595                 600                 605

Val Leu Val Ala Phe Arg Asp Met Val Ile Leu Lys Arg Tyr Glu Gly
610                 615                 620

Leu Lys Ala Thr Phe Ser Arg Leu Ser Leu Asp Ser Ile Asn Val Gly
625                 630                 635                 640
```

```
                        -continued

Ser Ser Ala Leu Ser Ile Thr Thr Lys Ser Ser Asn Ser Gly Arg
                645                 650                 655

Pro Ala Thr Ala Ala Ser Leu Asp Ala Gly Phe Gly Ser Tyr Asn Ser
            660                 665                 670

Gln Ser Ser Thr Leu Leu Asn Thr Ala Gly Ser Tyr Ser Ser Asp Ser
            675                 680                 685

Met Ser Asn Arg Ser Arg Ala Ala Ser Asn Thr Ser Ser Asn Pro Asp
    690                 695                 700

Gln Leu Ile Phe Gln Ser Phe Ser Ser Pro Asn Gln Arg Ala Thr Val
705                 710                 715                 720

Ile His Arg Ala Ser His Thr Ala Asp Thr Ser Gln Leu Ile Thr Glu
                725                 730                 735

Thr Val Gly Arg Met Leu Gln Cys Leu Ser Val Leu Ala Ser Val Gln
                740                 745                 750

Thr Gly Asp Glu Ala Gln Glu Lys Ile Glu Thr Leu Ser Lys Ala Leu
            755                 760                 765

Lys His Asn Trp Leu Gly Arg Gly Arg Thr Gly Arg Asp Arg Arg Gly
            770                 775                 780

Phe Val Gly Ala Lys Val Arg Pro Ser Ile Thr Thr His Thr Thr Ser
785                 790                 795                 800

Asp Asp Ser Met Asn Asp Pro Arg Asn Ser Asp Leu Gly Trp Gln Ile
                805                 810                 815

His Glu Gly Arg Gln Gln Val Ser Val Leu
            820                 825

<210> SEQ ID NO 11
<211> LENGTH: 1358
<212> TYPE: PRT
<213> ORGANISM: Neurospora crassa

<400> SEQUENCE: 11

Met Gly Leu Val Arg Pro His Arg Pro Ser Pro Gly Pro Val Arg Ile
1               5                   10                  15

Ile Ser Ala Ser Thr Ser Thr Ser Asp Asp Leu Thr Pro Leu Thr Ile
            20                  25                  30

Pro Arg Pro Ser Asp Gln Pro Thr Ala Pro Ser Pro Gln Pro Gly Gly
        35                  40                  45

Arg Pro Asp Ala Ser Gly Phe Gly Gly Arg Ala Gly Ala Ser Pro Glu
    50                  55                  60

Arg Arg Gly Gly Gly Thr Pro Thr Pro Gly Arg Glu Ser Ala
65                  70                  75                  80

Thr Pro Ile Tyr Ser Ser Phe Thr Ser Pro Ser Asn Ser Ala Ser Ala
                85                  90                  95

Pro Ser Leu Gln Thr Asn Phe Ser Arg Pro Thr Val Ser Thr Thr Ala
            100                 105                 110

Ala Leu Ser Thr Ala Arg Ser Val Ala Gly Thr Leu Ser Pro Ile Asp
        115                 120                 125

Thr Ala Pro Arg Asn Gly Pro Ser Pro Leu Thr Leu Pro Thr Ser
    130                 135                 140

Ala Thr Ser Thr Thr Ser Thr Ser Phe Ser Gly Arg Val Gly Val His
145                 150                 155                 160

Ser Arg Lys His Ser Ala Asn Ala Gly Leu Phe Glu Pro Thr Leu Pro
                165                 170                 175

Ser Thr Ser Thr Ser Asn Leu Asp Gln Ile Gln Ala Glu Ser Pro Lys
            180                 185                 190
```

```
Leu Ser Pro Thr Pro Ser Gln Ala Gln Arg Asp Met Ser Ala Ser His
        195                 200                 205

Ile Ala Ala Gln Ala Ala Val Ser Lys Ser Gln Leu Thr Gln Gln Gln
        210                 215                 220

Gln Gln Gln Gln Pro Gln Gln Gln Gln Gln Gln Gln Gln Gln Gln Gln
225                 230                 235                 240

Ala Pro Pro Phe Ala His Gln His Leu Val His Leu Gln His Arg Gln
                    245                 250                 255

Arg Ser Gln Thr Ile Pro Pro Ser Gly Glu His His Glu Gln Thr Ser
                260                 265                 270

Val Ala Asn Lys Arg Lys Ser Gly Gly Pro Met Ser Pro Pro Ile Leu
            275                 280                 285

Ser Leu Thr Glu Ala Ser Ala Pro Arg Asp Asn Val Phe Gly Ser Gln
        290                 295                 300

Gly Asn His Asn Gly Leu Ala Gly Asn His Thr Leu Ala Ala Thr Ala
305                 310                 315                 320

Ala Ala Asn Val Val Phe Pro Arg Ser Ala Gln Ser Ser Pro Lys Leu
                    325                 330                 335

Pro Ala Gln Pro Thr Asn Pro Leu Thr Pro Thr Pro Pro Val Ala
                340                 345                 350

Ala Glu Lys Pro Ala Val Lys Ser Glu Lys Ser Lys Val Lys Leu Phe
            355                 360                 365

Ser Arg Pro Gly Lys Ser Ser Lys Ala Glu Ser Ser Lys Glu Lys
        370                 375                 380

Pro Leu Pro Ser Pro Gly Lys Leu Gly His Ala Phe Ser Asn Leu Gln
385                 390                 395                 400

Arg Ala Asn Tyr Ser Thr Thr Ser Leu Glu Ser Asn Met Gln Gln Pro
                405                 410                 415

Phe Tyr Ala His Gly Asn Ser Ser Thr Ala Thr Ile Arg Pro Ala Glu
                420                 425                 430

Ala Thr Glu Lys Glu Val Lys Glu Lys Glu Lys Lys His Gly His Phe
            435                 440                 445

Leu Lys Arg Gln Lys Glu Lys Leu Ile Glu Ala Tyr His Leu Pro Leu
        450                 455                 460

Ser Ser Ala Ser Ser Asn Ser Arg Pro Thr Asp Pro Thr Ala Pro Ser
465                 470                 475                 480

Ser Leu Tyr Asn Phe Asn Leu Pro Thr Ser Pro Gly Pro Ser Ser Asn
                485                 490                 495

Ala Phe Lys Ser Gly Leu Asp Leu Arg His Gly Gly Arg Ala Leu Arg
            500                 505                 510

Glu Lys Lys Asn Lys Glu Asp Lys Ser Leu Asp Asp Ala Ala Ser Ser
        515                 520                 525

Tyr Asn Pro Gly Gly Asp Trp Pro Gly Pro Ser Ser Val Ser Ser Ala
        530                 535                 540

Thr Gly Asn Leu Ala Ser Ala Leu Phe His Asn Glu Pro Phe Asp Ser
545                 550                 555                 560

Gln Lys Phe Gly Leu Asn Asn Met Thr Leu Asp Asp Ala Trp Pro Phe
                565                 570                 575

Leu Arg Ala Lys Leu Leu Val Ile Phe Glu Ala Glu Asp Leu Arg Leu
                580                 585                 590

Pro Val Glu Asp Leu Asn Arg Ile Val Thr Met His Ile Gln Tyr Cys
            595                 600                 605
```

-continued

```
Ile Ser Arg Arg Ser Pro Asn Ile Ile Glu Asp Ile Arg Asp Phe
610                 615                 620

Leu Thr Thr Gly Phe Ser Ser Leu Asp Gln Ser Leu Lys Lys Thr Pro
625                 630                 635                 640

Glu Asp Arg Leu Ile Pro Ala Leu Val Glu Leu Trp Ile Phe Thr Phe
                645                 650                 655

Thr Ser Ile Leu Pro Tyr Leu Gln Ala Val Phe Leu Pro Leu Asp Met
                660                 665                 670

Glu Phe Ala Gly Asn Gly Pro Leu Met Thr Pro Asp Gln Ala Arg Asp
                675                 680                 685

Phe Trp Gly Gly Val Pro Ala Ser Tyr Gly Leu Ser Ile Ser Ala Ser
690                 695                 700

Ser Val Leu Asp Ile Arg Arg Leu Val Leu Leu Ala Phe Arg Asp Ile
705                 710                 715                 720

Val Ile Leu Pro Arg Tyr Asp Thr Leu Lys Ile Met Phe Ser Arg Leu
                725                 730                 735

Ser Leu Glu Phe Leu Pro Gln Ser Leu Ala Ser Met Ala Leu Ser Ser
                740                 745                 750

Pro Val Pro Val Pro Thr Ser Gly Phe Gln Asn Thr Ala His Asn Gln
                755                 760                 765

Gly Gly Ala Tyr Gln Pro Ala Leu Ser Thr Ser Pro Ser Gln Glu Ser
770                 775                 780

Gln Leu Ser Leu Ser Phe Ala Gly Ser Leu Pro Ala Thr Met Thr Leu
785                 790                 795                 800

Gly Met Gly Ala Gly Phe Gly Thr Ala Pro Pro Arg Pro Asn Thr Ser
                805                 810                 815

Met Ser Asn Pro Val Pro Ser Val Asp Pro Ser Tyr Ala Ser Tyr Asn
                820                 825                 830

Ser Asn Gly Met Gly Thr Ala Gly Gly Gly Asp Thr Pro Pro Gly
                835                 840                 845

Ser Gly Asn Arg Ser Arg Thr Ile Ser Asn Val Ser Phe Gly Ser Asp
850                 855                 860

His Gly Asn Ala Asn Arg Pro Phe Thr Pro Ser Ser Ile Gln Ala Leu
865                 870                 875                 880

Gly Ala Ala Ser Ala Gln Ala Ala Met Ser Thr Pro Ser Gly Val Gly
                885                 890                 895

Ile Ala Asn Leu Asn Leu Asn Met Ser Thr Pro Val Gln Gln Phe Pro
                900                 905                 910

Leu His Val Ala Pro Ser Ile Ala Ser Ile Gly Ser Asn Ser Ile His
                915                 920                 925

Gly Ser Leu Arg Asp Pro Thr Gly Gly Gly Gly Gly Arg Thr Ala
                930                 935                 940

Asp Gln Asn Val Glu Asp Ser Lys Gln Val Thr Glu Met Val Gly Arg
945                 950                 955                 960

Met Leu Gln Cys Met Ser Val Leu Ala Ser Val Ser Ala Pro Thr Thr
                965                 970                 975

Pro Ser Phe Thr Ser Ser Ile Pro Asn Gln Asn Pro His Ser Ser Thr
                980                 985                 990

Gly Asn Leu Thr Ser Tyr Asn Thr Tyr Ser Ser Ser Gln Asp Ser Val
                995                 1000                1005

Ala Thr Thr Thr Met Thr Asn Ala Thr Val Pro Ala Ser Pro Ser Gly
                1010                1015                1020
```

-continued

```
Ser Ser Val Ala Gly Gly Leu Pro Pro Leu Val Gln Thr Met Ser Ser
1025                1030                1035                1040

Pro Ser Gln Phe Ser Ser Pro Ser Ser Pro Ala Thr Pro Thr Ala Asn
                1045                1050                1055

Ser Pro Gly Pro Leu Pro Pro Arg Pro Ser Ile Ser Ser Leu Ser Ala
                1060                1065                1070

Ser Leu Ala Thr Ser Gly Ile Ser Gly Ala Gly Asn Asn Ser Leu Pro
            1075                1080                1085

Asn Thr Pro Thr Ala Ala Asn Ala Thr Thr Pro Thr Thr Pro Thr Ala
        1090                1095                1100

Pro Ala Asn Ala Ala Ala Gly Gly Gly Gly Gly Gly Gly Gly Gly Gly
1105                1110                1115                1120

Gly Ala Gly Gly Pro Gly Gly Gly Thr Gly Gly Tyr Gly Asn Val Pro
                1125                1130                1135

Pro Asp Glu Ser Ser Arg Met Ile Glu Glu Leu Asn Lys Leu Leu Lys
                1140                1145                1150

Leu Asn Trp Leu Gly Arg Gly Arg Thr Gly Arg Asn Arg Arg Gly Ile
            1155                1160                1165

Val Gly Gly Arg Val Lys Arg Ala Gly Ala Gly Ser Gly Ser Gly Ser
    1170                1175                1180

Ala Leu Ala Phe Ser Met Gly Ala Gly Ser Ala Gly Met Gly Tyr Ala
1185                1190                1195                1200

Ser Ser Ser Ser Tyr Gly Gly Tyr Ala Gly Gln Gly Gly Gly Gly Gly
                1205                1210                1215

Gly Gly Gly Gly Gly Gly Gly Gly Gly Gly Gly Gly Gly Tyr Ala Gly
                1220                1225                1230

Ser Leu Gly Thr Gly Pro Ala Gly Val Ser Met Asn Ser Leu Gly Thr
            1235                1240                1245

Thr Gly Thr Met Gly Ser Met Met Ser Ile Gly Thr Val Gly Ser Gly
    1250                1255                1260

Phe Gly Gly Gly Leu Leu Gln Gly Gln Gln Ala Glu Arg Asp Arg Gly
1265                1270                1275                1280

Gly Gly Gly Trp Thr Gly Thr Gly Thr Gly Ser Gly Leu Gly Thr Ser
                1285                1290                1295

Ala Ser Ile Ile Ala Gly Thr Thr Gly Thr Gly Gly Met Met Met Ser
            1300                1305                1310

Ser Leu Pro Ile Gly Ala Ser Val Ser Ala Thr Thr Ala Gly Thr Val
            1315                1320                1325

Gly Ala Gly Ala Ala Leu Ala Gly Ala Ala Gly Val Ser Met Pro Ala
    1330                1335                1340

Ala Ala Ala Gly Ser Leu Ser Asn Glu Ile Val Val Asp Asn
1345                1350                1355
```

HYPHAL GROWTH IN FUNGI

This is a continuation-in-part of application Ser. No. 09/275,549, filed Mar. 24, 1999 now U.S. Pat. No. 6,995,239.

FIELD OF THE INVENTION

The present invention generally relates to hyphal growth in fungi and in particular describes the modulation of genes associated with hyphal growth in filamentous fungi. The present invention provides methods and systems for the production of proteins and/or chemicals from filamentous fungi which comprise modulation of genes associated with hyphal growth.

BACKGROUND OF THE INVENTION

While the number of fungal species described is approximately 64,000, it is estimated that over one million species exist making this a diverse group of organisms. About 90% of fungi grow in the form of a radiating system of branching hyphae known as the mycelium. This mode of growth reflects a different life style from unitary organisms such as yeasts, with distinct advantages for advancing over surfaces and penetrating substrata (Carlile, 1994, The Growing Fungus, ed. Gow, N. A. R. & Gadd, G. M., Chapman & Hall, pp. 3–19). To date very few genes have been characterized which effect fungal branching. The most characterized gene is cot1 isolated from the fungus *Neurospora crassa*. Cot-1 is a temperature sensitive mutation leading to hyperbranching and the sequence, whose function is unknown, appears to encode a cAMP dependent protein kinase (Yarden et al, 1992, EMBO J. 11:2159–2166).

Filamentous fungi find industrial importance as producers of antibiotics, enzymes, fine chemicals and food (Aspergillus: 50 Years On (1994) vol 29, ed S. D. Martinelli & J. R. Kinghorn pp. 561–596). There remains a need in the art for improved methods of producing proteins in filamentous fungus. Filamentous fungus are also known pathogens of plants and animals. Therefore, understanding the genetic basis of fungal growth will provide insight regarding possible anti-fungal therapies.

SUMMARY OF THE INVENTION

The present invention is based, in part, upon the discovery of *Aspergillus* genes that are associated with fungal morphology and in particular with hyphal branching. A linear relationship between the degree of hyphal branching (measured as hyphal growth unit length) and culture viscosity in the fermentor (as measured by torque exerted on the rheometer impeller) has been observed. Isolation of hyper branching fungal mutants and identification of genes associated with fungal hyper branching provides a means for modulating fungal morphology thereby providing a means for controlling viscosity and improving fermentor performance.

The present invention is also based, in part, upon the identification of an *A. nidulans* mutant for the production of HbrA (the mutant being referred to herein as HbrA2) which exhibits a hyperbranching phenotype at the restrictive temperature, 42° C. The mutation HbrA2 does not appear to affect growth of *A. nidulans* at 26° C., but results in a hyperbranching, restricted growth phenotype at 42° C. The HbrA2 mutant comprising the heterologous nucleic acid encoding the *M. meihei* protease was able to secrete the protease at 26° C. The HbrA2 mutant was unable to secrete the protease at 37° C. but was able to secrete the endogenous alpha amylase at temperatures greater than 37° C. The present invention provides the amino acid, HbrA, and nucleic acid sequence for hbrA and methods for producing heterologous protein or chemicals in fungi by modulating the expression of proteins associated with hyphal growth, such as HbrA.

Accordingly, the present invention provides an isolated protein associated with hyphal growth in fungi having at least 70%, at least 75%, at least 80%, at least 85%, at least 90% or at least 95% identity to the amino acid sequence as disclosed in SEQ ID NO:2 or 8. In one embodiment, the protein associated with hyphal growth is HbrA which has the amino acid sequence as disclosed in SEQ ID NO:2. The present invention provides polynucleotides encoding the amino acid having the sequence as shown in SEQ ID NO:2 or 8 as well as polynucleotides having at least 60%, at least 65%, at least 70%, at least 75%, at least 80%, at least 85%, at least 90% or at least 95% identity to the polynucleotide having the sequence as shown in SEQ ID NO: 1 or 7. In one embodiment, the polynucleotide is capable of hybridizing to the polynucleotide having the sequence as shown in SEQ ID NO:1 or 7 under conditions of intermediate to high stringency, or is complementary to the polynucleotide having the sequence as shown in SEQ ID NO:1 or 7. In another embodiment, the polynucleotide has the nucleic acid sequence as disclosed in SEQ ID NO:1 or 7. The present invention also provides host cells and expression vectors comprising a polynucleotide encoding SEQ ID NO:2 or 8.

In one embodiment, the host cell is a fungus and in another is a filamentous fungus including *Aspergillus, Trichoderma, Mucor* and *Fusarium*. In yet a further embodiment, the *Aspergillus* species includes, but is not limited to, *A. niger, A. nidulans, A. oryzae* and *A. fumigatus*.

The present invention also provides a method for producing a desired protein in a fungus comprising the step of culturing a recombinant fungus comprising a polynucleotide encoding the desired protein under conditions suitable for the production of said desired protein, said recombinant fungus further comprising a polynucleotide encoding a protein associated with hyphal growth in said fungus said protein associated with hyphal growth having at least 70%, at least 75%, at least 80%, at least 85%, at least 90% or at least 95% identity to the amino acid sequence as disclosed in SEQ ID NO:2 or 8. In one embodiment, the polynucleotide encoding a protein associated with hyphal growth is homologous to said fungus and is present in amounts greater than found in the naturally occurring fungus. In another embodiment, the polynucleotide encoding a protein associated with hyphal growth is heterologus to said fungus and has been recombinantly introduced into said fungus. The method may further comprise the step of recovering said desired protein.

In another aspect of the present invention, it may be desirable to down regulate expression of the protein associated with hyphal growth in order to reduce culture viscosity. Accordingly, the present invention provides a method for producing a desired protein in a fungus comprising the step of culturing a recombinant fungus comprising a polynucleotide encoding the desired protein under conditions suitable for the production of said desired protein, said recombinant fungus comprising a mutation in an endogenous nucleic acid encoding a protein associated with hyphal growth said mutation resulting in the inhibition of the production by said fungus of the protein associated with hyphal growth.

In one embodiment, the polynucleotide encoding a protein associated with hyphal growth in said fungus comprises a replicating plasmid. In another embodiment, the polynucleotide encoding a protein associated with hyphal growth in said fungus is integrated into the fungal genome. In yet a further embodiment, the protein associated with hyphal growth has the amino acid sequence as shown in SEQ ID NO:2 or 8.

In yet a further embodiment of the present invention, the polynucleotide encoding a protein associated with hyphal growth has at least 60%, at least 65%, at least 70%, at least 75%, at least 80%, at least 85%, at least 90% or at least 95% identity to the polynucleotide having the sequence as shown in SEQ ID NO: 1 or 7, or is capable of hybridizing to the polynucleotide having the sequence as shown in SEQ ID NO:1 or 7 under conditions of intermediate to high stringency, or is complementary to the polynucleotide having the sequence as shown in SEQ ID NO:1 or 7. In another embodiment, the polynucletoide has the nucleic acid sequence as shown in SEQ ID NO: 1 or 7.

The present invention also provides a method for producing a recombinant fungus comprising a polynucleotide encoding a protein associated with hyphal growth comprising the steps of obtaining a polynucleotide encoding said protein associated with hyphal growth; introducing said polynucleotide into said host cell; and growing said host cell under conditions suitable for the production of said protein associated with hyphal growth. In one embodiment of this method, the host cell is a fungus. In another embodiment, the filamentous fungus includes *Aspergillus, Trichoderma, Mucor* and *Fusarium* species. In yet another embodiment, the *Aspergillus* species includes *A. niger, A. nidulans, A. oryzae* and *A. fumigatus*. In one embodiment, the polynucleotide has at least 60%, at least 65%, at least 70%, at least 75%, at least 80%, at least 85%, at least 90% or at least 95% identity to the nucleic acid having the sequence as shown in SEQ ID NO:1 or 7 or is capable of hybridizing to the polynucleotide having the sequence as shown in SEQ ID NO:1 or 7 under conditions of intermediate to high stringency, or is complementary to the polynucleotide having the sequence as shown in SEQ ID NO:1 or 7. In another embodiment, the polynucleotide has the sequence as shown in SEQ ID NO:1 or 7.

The present invention also relates to methods for screening for mutants exhibiting a hyper branching phenotype and which are capable of secreting heterologous protein. Accordingly, the present invention provides a method for the identification of hyper-branching mutants which comprise the steps of obtaining fungal mutants, subjecting said mutants to selection under desired conditions, and identifying mutants having the desired phenotypes. In one embodiment, the identification comprises selecting for hyphal growth. In yet another embodiment, identification comprises selecting for mutants capable of secreting protein. In another embodiment, the selection comprises growth and/or secretion of heterologous proteins at a restricted temperature.

BRIEF DESCRIPTION OF THE DRAWINGS

FIGS. 1A–1E illustrates the nucleic acid (SEQ ID NO:1, hbrA) and amino acid (SEQ ID NO:2) sequence for HbrA.

FIGS. 2A–2C illustrates an amino acid alignment of the amino acid sequence for (SEQ ID NO:2); *A. fumigatus* (SEQ ID NO:3); rat (SEQ ID NO:4) yeast slp gene (SEQ ID NO:5); *C. elegans* (SEQ ID NO:6).

FIG. 4A–4C illustrates the nucleic acid (SEQ ID NO:7, hbrB). The start codon is at position 1118 and the stop is at 3910. The ORF is 2793 in length and reads in the +2 reading frame. There are no introns.w FIG. 5 illustrates the amino acid (SEQ ID NO:8) sequence for HbrB.

FIG. 6A–6D illustrates an amino acid alignment of the amino acid sequence for HbrB; *Aspergillus nidulans* (*A. nid.*), *Aspergillus fumagatus* (*A. fum.*) and *Neurospora crassa* (SEQ ID NOS:8, 10 and 11, respectively). The homology of the *A. nidulans* HbrB with *N. crassa* is 36% (178/485). In *A. fumigatus* it is 53% (422/791).

DETAILED DESCRIPTION OF THE INVENTION

Definitions

Figure 3:
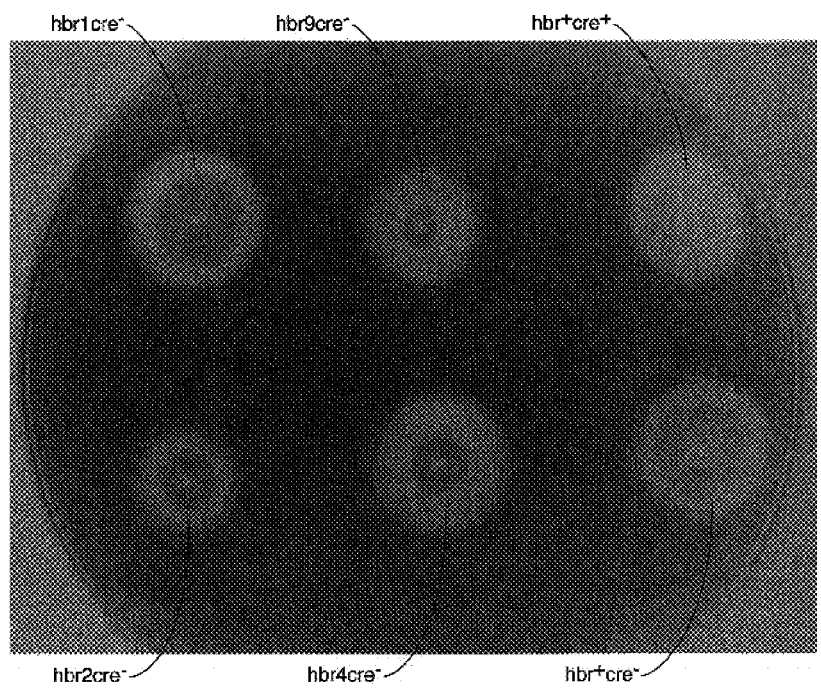
FIG. 3 illustrates amylase secretion by hbr/creA mutants.

As used herein, the phrase "protein associated with hyphal growth" refers to a protein which is capable of modulating hyphal growth in fungus. Illustrative of such proteins are the proteins HbrA 1–9 disclosed herein in the Examples. The term "HbrA" refers to the amino acid sequence as shown in SEQ ID NO:2. The term "hbrB," "HbrA3" and "hbr3" are used interchangeably herein. The present invention encompasses proteins associated with hyphal growth in fungus having at least 70%, at least 75%, at least 80%, at least 85%, at least 90% or at least 95% identity to the amino acid sequence as disclosed in SEQ ID NO:2 or SEQ ID NO:8. Percent identity at the nucleic acid level is determined using the FastA program and percent identity at the amino acid level is determined using the TFastA both of which use the method of Pearson and Lipman (PNAS USA, 1988, 85:2444–2448). The present invention also encompasses mutants, variants and derivatives of HbrA or HbrB as long as the mutant, variant or derivative is capable of modulating hyphal growth in fungus.

As used herein, "nucleic acid" refers to a nucleotide or polynucleotide sequence, and fragments or portions thereof, and to DNA or RNA of genomic or synthetic origin which may be double-stranded or single-stranded, whether representing the sense or antisense strand. As used herein "amino acid" refers to peptide or protein sequences or portions thereof.

The terms "isolated" or "purified" as used herein refer to a nucleic acid or amino acid that is removed from at least one component with which it is naturally associated.

As used herein, the term "heterologous" when referring to a protein associated with hyphal growth refers to a protein that does not naturally occur in a fungal cell. The term "homologous" when referring to a protein associated with hyphal growth refers to a protein native or naturally occurring in the fungus. The invention includes fungal host cells producing the homologous protein associated with hyphal growth at higher copy number than found in the naturally occurring fungal host and produced at a higher copy level via recombinant DNA technology.

As used herein, the term "overexpressing" when referring to the production of a protein in a host cell means that the protein is produced in greater amounts than its production in its naturally occurring environment.

DESCRIPTION OF THE PREFERRED EMBODIMENTS

The present invention relates to the identification of HbrA and HbrB in *A. nidulans*. The mutation of HbrA, referred to herein as HbrA2, was assigned to chromosome VII by parasexual analysis (*Aspergillus:* 50 Years On (1994) vol 20, ed S. D. Martinelli & J. R. Kinghorn pp. 41–43). At 37° C., mutant hbrA2, unlike wild-type *A. nidulans*, fails to secrete recombinantly expressed *M. meihei* protease. The translated sequence of the hbrA2 gene shows significant identity with the yeast SLP/VPS33 Sec1 gene product. Available evidence indicates that SLPNPS33 Sec1 encodes a protein essential for vacuolar protein sorting. SLP1 mutants fail to direct proteins to the vacuoles, and they are sent along a default pathway to the cytoplasmic membrane. The exact nature and function of the SLP1/VPS33 Sec1 protein is unknown, but it is a member of the SEC1 family, and may be a membrane associated protein involved in directing vesicles to vacuoles. Deletion of VPS33 in yeast in not lethal, but leads to slow growth, temperature sensitivity, and loss of vacuoles as revealed by staining light and electron microscopy. Fluorescence microscopy has shown that like SLP1/VSP33 mutants in yeast, HbrA2 is defective in vacuole assembly at the non-permissive temperature.

The mutation HbrA2 does not appear to affect growth of A. nidulans at 26° C., but results in a hyperbranching, restricted growth phenotype at 42° C. The hyperbranching phenotype shows extensive branching in the apical compartment, unlike the wild-type A. nidulans. The mutant grows slowly at the non-permissive temperature giving rise to highly compact colonies on agar media. Mucor meihei protease was transformed into wild-type A. nidulans and crossed into either the hbrA2 or hbrB3 mutant. The hbrA2 or hbrB3 mutants comprising the heterologous nucleic acid encoding the M. meihei protease were able to secrete the protease at 26° C. The hbrA2 and hbrB3 mutants were unable to secrete the protease at 37° C. but was able to secrete the endogenous alpha amylase at temperatures greater than 37° C.

In view of the observation that hbrA mutants are incapable of producing foreign protein, it appears that genetically engineering fungal hosts to modulate the expression of proteins associated with hyphal growth, in particular, mutants HbrA1–9, would provide a means for enhancing the production of proteins or chemicals in the fungal host. In one aspect of the present invention, it would be desirable to increase expression of proteins associated with hyphal growth. In another aspect of the present invention, it would be desirable to decrease or eliminate expression of proteins associated with hyphal growth by means known to the skilled artisan.

I. HbrA amino acid and hbrA nucleic acid Sequences

The present invention provides the amino acid (SEQ ID NO:2) HbrA and nucleic acid (SEQ ID NO:1) sequence for hbrA. The present invention encompasses amino acid variants having at least 70% identity to the amino acid having the sequence as shown in SEQ ID NO:2 as long as the variant is capable of modulating hyphal growth. Percent identity at the nucleic acid level is determined using the FastA program and percent identity at the amino acid level is determined using the TFastA both of which use the method of Pearson and Lipman (PNAS USA, 1988, 85:2444–2448). Alternatively, identity is determined by MegAlign Program from DNAstar (DNASTAR, Inc. Maidson, Wis. 53715) by Jotun Hein Method (1990, Method in Enzymology, 183: 626–645) with a gap penalty=11, a gap length penalty=3 and Pairwise Alignment Parameters Ktuple=2. As the skilled artisan will readily recognize, a variety of polynucleotides can encode HbrA. The present invention encompasses all such polynucleotides. HbrA, and other polynucleotides encoding proteins associated with hyphal growth, may be obtained by standard procedures known in the art from, for example, cloned DNA (e.g., a DNA "library"), genomic DNA libraries, by chemical synthesis once identified, by cDNA cloning, or by the cloning of genomic DNA, or fragments thereof, purified from a desired cell. (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. 1, 11.) Nucleic acid sequences derived from genomic DNA may contain regulatory regions in addition to coding regions. Whatever the source, the isolated polynucleotide encoding the protein associated with hyphal growth can be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the gene may be accomplished in a number of ways. For example, a polynucleotide encoding a protein associated with hyphal growth or its specific RNA, or a fragment thereof, such as a probe or primer, may be isolated and labeled and then used in hybridization assays to detect related genes. (Benton, W. and Davis, R., 1977, Science 196:180; Grunstein, M. And Hogness, D., 1975, Proc. Natl. Acad. Sci. USA 72:3961). Those DNA fragments sharing substantial sequence similarity to the probe will hybridize under stringent conditions.

Also included within the scope of the present invention are fungal microorganism polynucleotide sequences that are capable of hybridizing to the nucleotide sequence of SEQ ID NO:1 or 7 under conditions of intermediate to maximal stringency. Hybridization conditions are based on the melting temperature (Tm) of the nucleic acid binding complex, as taught in Berger and Kimmel (1987, Guide to Molecular Cloninq Techniques, Methods in Enzymology, Vol 152, Academic Press, San Diego Calif.) incorporated herein by reference, and confer a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate or low stringency hybridization can be used to identify or detect polynucleotide sequence homologs.

The term "hybridization" as used herein shall include "the process by which a strand of nucleic acid joins with a complementary strand through base pairing" (Coombs J (1994) Dictionary of Biotechnology, Stockton Press, New York N.Y.).

The process of amplification as carried out in polymerase chain reaction (PCR) technologies is described in Dieffenbach CW and GS Dveksler (1995, PCR Primer, a Laboratory Manual, Cold Spring Harbor Press, Plainview N.Y.). A nucleic acid sequence of at least about 10 nucleotides and as many as about 60 nucleotides from SEQ ID NO:1 preferably about 12 to 30 nucleotides, and more preferably about 20–25 nucleotides can be used as a probe or PCR primer.

Expression Systems

The present invention provides host cells, expression methods and systems for the production of desired proteins in host fungus. Once nucleic acid encoding a protein associated with hyphal growth is obtained, recombinant host cells containing the nucleic acid may be constructed using techniques well known in the art. Molecular biology techniques are disclosed in Sambrook et al., Molecular Biology Cloning: A Laboratory Manual, Second Edition (1989) Cold Spring Harbor Laboratory Press, Cold Spring Harbor, N.Y. (1989). Nucleic acid encoding proteins associated with hyphal growth and having at least 60% identity to hbrA is obtained and transformed into a host cell using appropriate vectors. A variety of vectors and transformation and expression cassettes suitable for the cloning, transformation and expression in fungus are known by those of skill in the art.

Typically, the vector or cassette contains sequences directing transcription and translation of the nucleic acid, a selectable marker, and sequences allowing autonomous replication or chromosomal integration. Suitable vectors comprise a region 5' of the gene which harbors transcriptional initiation controls and a region 3' of the DNA fragment which controls transcriptional termination. These control regions may be derived from genes homologous or heterologous to the host as long as the control region selected is able to function in the host cell.

Initiation control regions or promoters, which are useful to drive expression of the protein associated with hyphal growth in a host cell are known to those skilled in the art. Virtually any promoter capable of driving these proteins is suitable for the present invention. Nucleic acid encoding the protein is linked operably through initiation codons to selected expression control regions for effective expression of the protein. Once suitable cassettes are constructed they are used to transform the host cell.

General transformation procedures are taught in Current Protocols In Molecular Biology (vol. 1, edited by Ausubel et al., John Wiley & Sons, Inc. 1987, Chapter 9) and include calcium phosphate methods, transformation using PEG and electroporation. For *Aspergillus* and *Trichoderma*, PEG and Calcium mediated protoplast transformation can be used (Finkelstein, DB 1992 Transformation. In Biotechnology of Filamentous Fungi. Technology and Products (eds by Finkelstein & Bill) 113–156. Electroporation of protoplast is disclosed in Finkelestein, DB 1992 Transformation. In Biotechnology of Filamentous Fungi. Technology and Products (eds by Finkelstein & Bill) 113–156. Microprojection bombardment on conidia is described in Fungaro et al. (1995) Transformation of *Aspergillus nidulans* by microprojection bombardment on intact conidia. FEMS Microbiology Letters 125 293–298. *Agrobacterium* mediated transformation is disclosed in Groot et al. (1998) *Agrobacterium tumefaciens*-mediated transformation of filamentous fungi. Nature Biotechnology 16 839–842.

Host cells which comprise the sequence for hbrA and express the protein may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein. For production of a desired protein in a fungal host cell, an expression vector comprising at least one copy of nucleic acid encoding a desired protein is transformed into the recombinant host cell comprising nucleic acid encoding a protein associated with hyphal growth and cultured under conditions suitable for expression of the protein. Examples of desired proteins include enzymes such as hydrolases including proteases, cellulases, amylases, carbohydrases, and lipases; isomerases such as racemases, epimerases, tautomerases, or mutases; transferases, kinases and phophatases along with proteins of therapeutic value. Alternatively, it may be advantageous to down-regulate or mutate proteins associated with hyphal growth in order to reduce the viscosity in the fermentor.

III Vector Sequences

Expression vectors used in expressing the hprA in fungal cells or the desired protein in fungal cells comprise at least one promoter associated with the protein which promoter is functional in the host cell. In one embodiment of the present invention, the promoter is the wild-type promoter for the protein and in another embodiment of the present invention, the promoter is heterologous to the protein, but is still functional in the fungal host cell. In one preferred embodiment of the present invention, nucleic acid encoding the protein is stably integrated into the microorganism genome.

In a preferred embodiment, the expression vector contains a multiple cloning site cassette which preferably comprises at least one restriction endonuclease site unique to the vector, to facilitate ease of nucleic acid manipulation. In a preferred embodiment, the vector also comprises one or more selectable markers. As used herein, the term selectable marker refers to a gene capable of expression in the host which allows for ease of selection of those hosts containing the vector.

IV. Assay of the Activity of Proteins Associated with Fungal Growth

The results shown in Examples I and II illustrate the use of a temperature based screen to identify mutants which effect fungal branching. The unexpected advantage of using such a temperature based screen is the ability to identify HbrA mutants or mutants of proteins associated with hyphal growth having a differential effect on the export of native or endogenous genes vs the export of recombinantly introduced heterologous protein. This type of screening method facilitates the isolation of strains which are capable of increased secretion of heterologous protein. Therefore, the present invention also provides a method for the identification of hyper-branching mutants which enhance protein secretion comprising the steps of obtaining fungal mutants, subjecting said mutants to selection under desired conditions, and identifying the desired mutants. In one embodiment, the identification comprises selecting for hyphal growth. In another embodiment, the selection comprises growth and/or secretion of heterologous proteins at a restricted temperature.

EXAMPLES

Example 1

This example illustrates the isolation of the hbrA gene. In order to isolate the hbrA gene, DNA was prepared from pooled cosmids of the chromosome-sorted cosmid library of wild-type DNA from *A. nidulans* obtained from FGSC (Funal Genetic Stock Center, Department of Microbiology University of Kansas Medical Center, Kansas City, Kans. 66160). 5 pools of 20 cosmids each were used in transformation experiments. In order to assess transformation efficiency, an hbrA2, argB double mutant was used as a recipient for cotransformation using a mixture of cosmid DNA and transforming vector Arp, which carries the argB gene and a replicating sequence. After transformation, protoplasts were regenerated and selected on medium lacking arginine at 42° C. One of the cosmid pools gave rise to a few strongly growing, normally conidiating colonies in a background of Arg+Hbr-transformants. The pool was subdivided into 4 pools of 5 cosmids, and transformation repeated. A single cosmid was isolated which was able to complement the hbrA2 mutation, restoring wild-type growth. Sub-cloning of the cosmid led to identification of an EcoRI fragment carrying the transforming sequence. The EcoRI/BamHI fragments failed to complement the mutation suggesting that the BamHI site lies within the hbrA gene. The fragment was isolated and subjected to nucleic acid sequencing. The nucleic acid and amino acid sequence for the hbrA gene is shown in FIGS. 1A–1D. Table I shows protease activity for Hbr2, as well as other identified hyper-branching mutants at the permissive and non-permissive temperatures.

TABLE I

| Strain | Mean Protease Activity (units/gram of biomass) at 26 C. | | Mean Protease Activity (units/gram of biomass) at (37 C.) | |
|---|---|---|---|---|
| | 48 hrs | 72 hrs | 48 hrs | 72 hrs |
| Wild-type | 963 +/− 57 | 703 +/− 12 | 380 +/− 44 | 339 +/− 40 |
| HbrA2 | 857 +/− 18 | 1237 +/− 155 | 0 +/− 0 | 0 +/− 0 |
| Hbr3 | 689 +/− 76 | 1194 +/− 234 | 0 +/− 0 | 0 +/− 0 |
| Hbr6 | 0 +/− 0 | 1892 +/− 122 | 0 +/− 0 | 0 +/− 0 |
| Hbr8 | 0 +/− 0 | 2165 +/− 156 | 0 +/− 0 | 487 +/− 10 |

These findings indicate that a previously uncharacterized filamentous fungal gene hbrA plays a role in heterologous protein export.

Example 2

This Example describes the characterization of hyper-branching mutants of *A. nidulans*. Below is Table II which shows the chromosomal location of the hbr mutants.

| hbr Mutant | Chromosomal location |
|---|---|
| hbr1 | I |
| hbrA2 | VII |
| hbr3 | I |
| hbr4 | III |
| hbr5 | VIII |
| hbr6 | III |
| hbr7 | III |
| hbr8 | I |
| hbr9 | III |

All mutations were recessive and unlinked to each other and represent previously uncharacterized mutations which effect fungal hyperbranching and protein secretion. The ability of hbrA2 mutant to secrete the endogenous protein alpha amylase at 37° C. was examined by growing the hbrA2:creA-double mutant on petri dishes with starch as the sole carbon source (the CreA gene is a negatively acting regulator of carbon catabolism repression. Mutations of CreA (CreA-) causes carbon catabolism derepression of enzymes such as alpha amylase). The hbrA2:creA-double mutant like the hbrA+:creA- was shown to be capable of secreting the endogenous protein alpha amylase, see FIG. 3. These results indicate the hbrA gene unexpectantly plays a role in heterologous protein secretion.

The hbr3 mutant, like the hbrA2 mutant, produces slightly higher *M. meihei* protease than the wild-type at 26° C. At 37° C., the hbr3 mutant like the hbrA2 mutant does not produce the *M. meihei* protease. The hbrA2 mutation is located on chromosome VII, the hbr3 mutation is located on chromosome 1. These results indicate that the hbr3 gene product also plays a role in heterologous protein export. Therefore, modulation of the expression of the wild-type hbr3 gene product would appear to be advantageous in increasing heterologous protein export.

The hbr6 and hbr8 mutations which are located on chromosomes III and I respectively, produce significantly higher levels of *M. meihei* protease than the wild-type at 26° C. and would appear to increase the secretion of heterologous protein in a filamentous fungus grown in the temperature range around 26° C. Therefore, modulation of expression of the wildtype hbr6 and hbr8 gene products would also appear to have utility in increasing heterolgous protein export. Mutant versions of the hbr6 and hbr8 genes have no or significantly less *M. meihei* secretion than the wild-type as shown by Table III.

TABLE III

| Strain | Mean Protease Activity (units/gram of biomass) at 26 C. | | Mean Protease Activity (units/gram of biomass) at 37 C. | |
|---|---|---|---|---|
| | 48 hrs | 72 hrs | 48 hrs | 72 hrs |
| Wild-type | 963 +/− 57 | 703 +/− 12 | 380 +/− 44 | 339 +/− 40 |
| hbr5 | 46 +/− 60 | 1152 +/− 133 | 533 +/− 53 | 1648 +/− 797 |
| hbr7 | 0 +/− 0 | 1098 +/− 53 | 580 +/− 60 | 1581 +/− 660 |
| hbr4 | 844 +/− 114 | 1688 +/− 67 | 343 +/− 26 | 260 +/− 15 |
| hbr9 | 0 +/− 0 | 268 +/− 16 | 0 +/− 0 | 1562 +/ 641 |

Table II illustrates that *M. meihei* protease secretion in the hbr5 and hbr7 mutants yields slightly more protease at 26° C. after 72 hours compared to the wild-type, and significantly more protease at 72 hours at 37° C.

The hbr4 mutant produced significantly more *M. meihei* protease than the wild-type after 72 hours at 26° C. but significantly less protease after 72 hours at 37° C. However, the hbr4:creA-double mutant produced significantly higher levels of alpha amylase/unit area fungal colony that the wild-type strain containing only the creA-mutation. These results indicate a significant role for the hbr4 gene product not only in terms of fungal morphology increasing native protein secretion but also a role for this gene product in heterologous protein export.

The hbr9 mutation exhibited poor expression of *M. meihei* protease at 26° C., but significantly higher levels of *M. meihei* protease and alpha amylase/unit area fungal colony than the wild-type.

Example 3

This example illustrates the isolation and characterization of the hbrB gene.

Using the procedures of Example 1, the hbrB gene was isolated and sequenced. The nucleic acid and amino acid sequence for the hbrB gene is shown in FIGS. 4–6. For clarity, hbrB is the gene and hbrB3 is the temperature sensitive mutation of the gene which causes the hyper-branching phenotype.

3.1 Promoter Replacement

A promoter exchange was undertaken using the conditionally expressed gene, alcA. 1050 bp of the 5' end of hbrB was ligated behind the alcA promoter in the expression vector pAL3 (Waring, et al. Gene 79:119–130). This was transformed into the *A. nidulans* wild type strain, G191. 25 transformants were obtained, 5 of which showed controllable morphology on different media. Calcofluor staining was used to study the phenotypic effects of downregulating hbrB. The downregulated phenotype differs from that of the original temperature sensitive mutation. The spore and first intercalary compartments are extremely swollen and resemble that of a loss of polarity phenotype. A Southern blot was carried out to check integration and one transformant, T12, showed the correct integration pattern.

1.2 Sexual Cross between 2–169 and T12.

To test whether the DNA sequence which complements hbrB3 is the hbrB gene itself or an extragenic suppressor recombination between the two genes was performed. To do this, the original temperature sensitive mutant, 2–169, was crossed with the T12 promoter replacement strain. If the two genes are at the same locus, no recombination will occur between them and all progeny will either be temperature sensitive or repressed on glucose. Alternatively, if the complementing gene is an extragenic suppressor it will recombine freely with hbrB, producing progeny of four phenotypic classes. The two parental classes will be obtained; a wild type class and a class in which the strain is both temperature sensitive and alcA controlled will result. 120 progeny were tested and only the two parental classes were obtained in an approximate 1:1 ratio, indicating that hbrB and hbrB3 are at the same locus.

1.3 Extracellular protease production in hbrB3.

The Sod$^{VI}$C1 mutation in *A. nidulans* affects processing of secretory proteins destined for the cell surface and beyond (Lee, H. et al (2002) FEMS Microbiol. Left. 208: 253–257). The Sod$^{VI}$C gene is an ∝-COP related gene which is essential for intracellular protein transport between membrane bound components of the secretory pathway and is essential for polarised growth (Whittaker, S. et al. (1999) Fungal Genetics and Biology 26:236–252). The Sod$^{VI}$C1 mutant strain is defective in the ability to secrete extracellular protease as shown by the failure to produce a halo on a 1% skim milk agar plate. To ascertain whether HbrB has a similar role which was suggested by the PSI-Blast results, wild type and hbrB3 strains were inoculated onto similar skim milk plates and were incubated at the restrictive temperature (42° C.). Both strains produced halos suggesting the hbrB3 mutation has no detrimental effect on protein secretion.

We claim:

1. An isolated polynucleotide encoding the amino acid having the sequence as shown in SEQ ID NO: 8.

2. An isolated polynucleotide having at least 95% identity to the polynucleotide having the sequence as shown in SEQ ID NO:7, or is capable of hybridizing to the polynucleotide having the sequence as shown in SEQ ID NO: 7 under conditions of intermediate to high stringency, or is complementary to the polynucleotide having the sequence as shown in SEQ ID NO:7, wherein the isolated polynucleotide encodes an amino acid having the sequence of SEQ ID NO:8.

3. The isolated polynucleotide of claim 2 having the nucleic acid sequence as disclosed in SEQ ID NO:7.

4. An expression vector comprising the polynucleotide of claim 1.

5. A host cell comprising the expression vector of claim 4.

6. The host cell of claim 5 that is a filamentous fungus.

7. The host cell of claim 6 wherein said filamentous fungus is *Aspergillus*, *Trichoderma*, *Mucor* or *Fusarium*.

8. A method producing a desired protein in a fungus comprising the steps of, culturing a recombinant fungus comprising a polynucleotide encoding a desired protein under conditions suitable for the production of said desired protein, said recombinant fungus further comprising a polynucleotide encoding a protein associated with hyphal growth in said fungus said protein having at least 95% identity to the amino acid sequence as disclosed in SEQ ID NO:8, wherein said polynucleotide encoding the protein associated with hyphal growth is homologous to said fungus said polypeptide being present in copy number greater than found in the naturally occurring fungus and producing the desired protein.

9. The method of claim 8 further comprising the step of recovering said desired protein.

10. A method for producing a desired protein in a fungus comprising the steps of,
culturing a recombinant fungus comprising a polynucleotide encoding a desired protein under conditions suitable for the production of said desired protein, said recombinant fungus further comprising a polynucleotide encoding a protein associated with hyphal growth in said fungus said protein having at least 95% identify to the amino acid sequence as disclosed in SEQ ID NO:8, wherein said polynucleotide encoding the protein associated with hyphal growth is heterologous to said fungus said and has been recombinantly introduced into said fungus and producing the desired protein.

11. The method of claim 8 wherein said polynucleotide encoding a protein associated with hyphal growth in said fungus comprises a replicating plasmid.

12. The method of claim 8 wherein said polynucleotide encoding a protein associated with hyphal growth in said fungus is integrated into the fungal genome.

13. The method of claim 8 wherein said protein associated with hyphal growth has the amino acid sequence as shown in SEQ ID NO:8.

14. The method of claim 8 wherein said polynucleotide encoding a protein associated with hyphal growth has 60% identity to the polynucleotide having the sequence as shown in SEQ ID NO:7, or is capable of hybridizing to the polynucleotide having the sequence as shown in SEQ ID NO:7 under conditions of intermediate to high stringency, or is complementary to the polynucleotide having the sequence as shown in SEQ ID NO:7.

15. The method of claim 8 wherein said polynucleotide has the nucleic acid sequence as shown in SEQ ID NO:7.

16. The method of claim 8 wherein said fungus is a filamentous fungus.

17. The method of claim 16 wherein said filamentous fungus is *Aspergillus, Trichoderma, Mucor* or *Fusarium* species.

18. The method of claim 17 wherein the *Aspergillus* is *A. niger, A. nidulans, A. oryzae* or *A. fumigatus*.

19. A method for producing a recombinant fungus comprising a polynucleotide encoding a protein associated with hyphal growth comprising the steps of:
(a) obtaining a polynucleotide encoding said protein associated with hyphal growth and said protein having at least 95% identity to the amino acid sequence of SEQ ID NO:8;
(b) introducing said polynucleotide into said host cell; and
(c) growing said host cell under conditions suitable for the production of said protein associated with hyphal growth.

20. The method of claim 19 wherein said host cell is a filamentous fungal cell.

21. The method of claim 20 wherein said filamentous fungal cell is *Aspergillus, Trichoderma, Mucor,* or *Fusarium*.

22. The method of claim 21 wherein said *Aspergillus* is *A. niger, A. nidulans, A. oryzae* or *A. fumigatus*.

23. A method for producing a desired protein in a fungus comprising the steps of
culturing a recombinant fungus comprising a polynucleotide encoding the desired protein under conditions suitable for the production of said desired protein, said recombinant fungus comprising a mutation in an endogenous nucleic acid encoding a protein associated with hyphal growth said mutation resulting in the inhibition of the production by said fungus of the protein associated with hyphal growth, wherein said protein associated with hyphal growth has at least 95% identity to the amino acid sequence of SEQ ID NO:8, and producing the desired protein.

24. The method of claim 10 further comprising the step of recovering said desired protein.

25. The method of claim 23 further comprising the step of recovering said desired protein.

26. The method of claim 10 wherein said polynucleotide encoding a protein associated with hyphal growth in said fungus comprises a replicating plasmid.

27. The method of claim 10 wherein said polynucleotide encoding a protein associated with hyphal growth in said fungus is integrated into the fungal genome.

28. The method of claim 10 wherein said protein associated with hyphal growth has the amino acid sequence as shown in SEQ ID NO:8.

29. The method of claim 10 wherein said polynucleotide has the nucleic acid sequence as shown in SEQ ID NO: 7.

30. The method of claim 10 wherein said fungus is a filamentous fungus.

31. The method of claim 30 wherein said filamentous fungus is *Aspergillus, Trichoderma, Mucor* or *Fusarium*.

32. The method of claim 31 wherein the *Aspergillus* is *A. niger, A. nidulans, A. oryzae* or *A. fumigatus*.

33. The method of claim 31 wherein said filamentous fungus is *Trichoderma*.

34. The method of claim 10 wherein the desired protein is an enzyme.

35. The method of claim 10 wherein the desired protein is a therapeutic protein.

36. The method of claim 23 wherein said protein associated with hyphal growth has the amino acid sequence as shown in SEQ ID NO:8.

* * * * *